(12) United States Patent
Parsons et al.

(10) Patent No.: US 8,216,851 B2
(45) Date of Patent: Jul. 10, 2012

(54) CHARACTERIZATION OF N-GLYCAN MIXTURES BY NUCLEAR MAGNETIC RESONANCE

(75) Inventors: Ian Christopher Parsons, Belmont, MA (US); Jonathan Lansing, Reading, MA (US); Daniela Beccati, Boston, MA (US); Scott Bailey, Somerville, MA (US); Carlos J. Bosques, Arlington, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 81 days.

(21) Appl. No.: 12/595,940

(22) PCT Filed: Apr. 15, 2008

(86) PCT No.: PCT/US2008/060328
§ 371 (c)(1),
(2), (4) Date: Feb. 25, 2010

(87) PCT Pub. No.: WO2008/128218
PCT Pub. Date: Oct. 23, 2008

(65) Prior Publication Data
US 2010/0279269 A1    Nov. 4, 2010

Related U.S. Application Data

(60) Provisional application No. 60/923,686, filed on Apr. 16, 2007.

(51) Int. Cl.
*C12Q 1/25* (2006.01)
*G01R 33/44* (2006.01)
*G01R 33/20* (2006.01)
*G01R 33/00* (2006.01)

(52) U.S. Cl. ............. 436/173; 435/4; 324/307; 324/300

(58) Field of Classification Search .................. 436/173; 435/4; 324/307, 300
See application file for complete search history.

(56) References Cited

U.S. PATENT DOCUMENTS
2006/0127950 A1    6/2006 Bosques et al.

FOREIGN PATENT DOCUMENTS
WO    WO-2007012695 A2    2/2007

OTHER PUBLICATIONS

Pace, et al., "Characterization of Minor N-linked Glycans on Antibodies Using Endo H Release and MALDI-Mass Spectrometry," Analytical Letters, 42: 1711-1724, 2009.
Nilsson et al. "New methods for misture analysis by liquid state NMR" EPSRC reference: EP/E05899x/1, 2007.

(Continued)

*Primary Examiner* — Christine T Mui
(74) *Attorney, Agent, or Firm* — Choate Hall & Stewart LLP; Brenda Herschbach Jarrell; Jessica Russell Colantonio

(57) ABSTRACT

The present disclosure provides nuclear magnetic resonance (NMR) methods for characterizing mixtures of N-linked glycans. Without limitation, methods of the present disclosure may be useful in characterizing monosaccharide composition, branching, fucosylation, sulfation, phosphorylation, sialylation linkages, presence of impurities and/or efficiency of a labeling procedure (e.g., labeling with a fluorophore such as 2-AB). In certain embodiments, the methods can be used quantitatively. In certain embodiments, the methods can be combined with enzymatic digestion to further characterize glycan mixtures.

54 Claims, 27 Drawing Sheets

OTHER PUBLICATIONS

Biospin et al, "An unambiguous assignment method by 2D selective-TOCSY-HSQC and selective-TOCSY-DQFCOSY and structural analysis by selective-TOCSY-NOESY experiments of biantennary undecasaccharide" Carbohydrate Research, (2005) vol. 240, pp. 469-479.

Di Patrizi, et al, "Structural Characterization of the N-glycans of gpMuc from Mucuna pruriens seeds" Glycoconjugate Journal, vol. 23, No. 7-8, (Nov. 2006), pp. 599-609.

Hokke et al., "Structural analysis of the sialylated N- and O-linked carbohydrate chains of recominant human erythropoeitin expressed in Chinses hamster ovary cells. Sialylation patters and branch location of dimeric N-acetyllactosamine units" European Journal of Biochemistry, vol. 228, pp. 981-1008, 1995.

International Search Report for PCT/US2008/060328.

Manzi et al, "Exploring The glycan repertoire of genetically modified mice by isolation and profiling of the major glycan classes and nano-NMR analysis of glycan mixtures" Glycobiology, vol. 10, No. 7, Jul. 2000, pp. 669-689.

Nishimura et al, "Structure of netural branced xylooligosaccharides produced by xylanase from in situ reduced hardwood xylan" Carbohydrate Research, Elsevier Scientific Publishing Company, (1998) vol. 308, No. 1-2, 1, pp. 117-122.

Mandal et al., "A Comprehensive Discussion of HSQC and HMQC Pulse Sequences" Concepts in Magnetic Resonance, (2004), Part A, vol. 20A, pp. 1-24.

Ortner et al., "Analysis of glycans in glycoproteins by diffusion-ordered nuclear magnetic resonance spectroscopy" Anal Bioanal Chem, (2007), vol. 388, pp. 173-177.

Nilsson et al. "New methods for misture analysis by liquid state NMR" EPSRC reference: EP/E05899x/1, 1997.

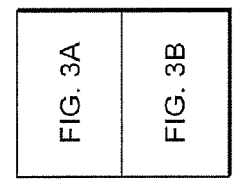
FIG. 3
Monosialo (2,6) biantennary + Fuc (A1F)
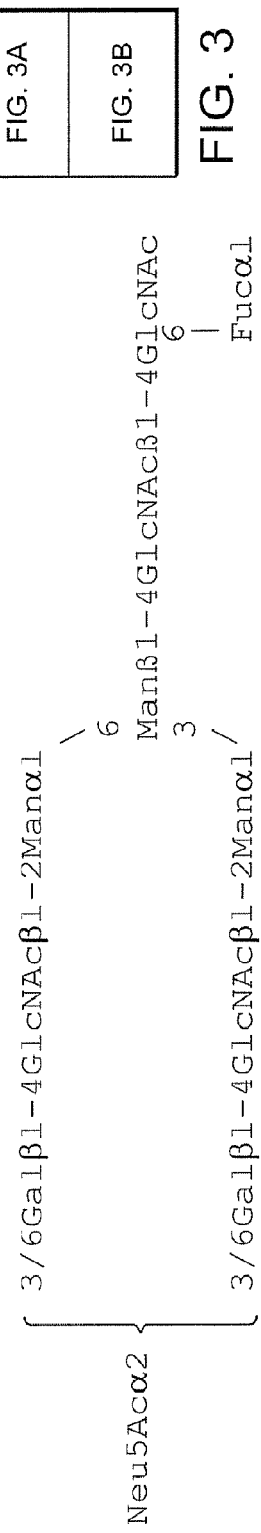
Asialo, galactosylated, triantennary (NA3)
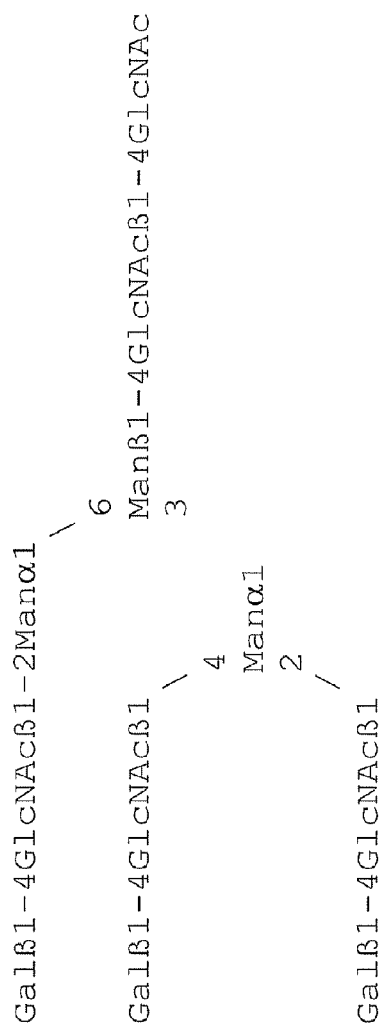
FIG. 3A

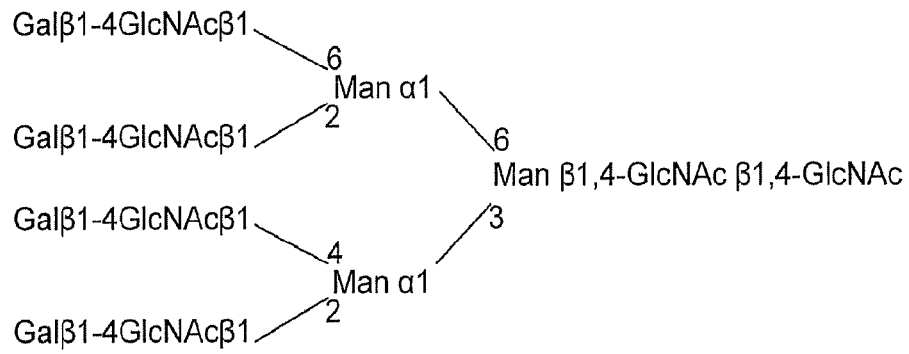
NA4 N-linked oligosaccharide    FIG. 4A
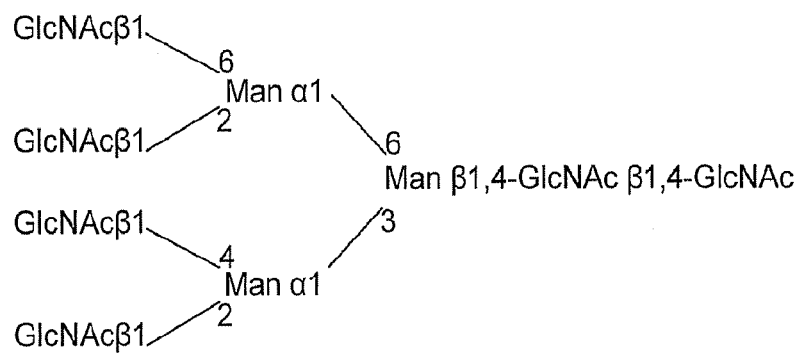
NGA4 N-linked oligosaccharide    FIG. 4B
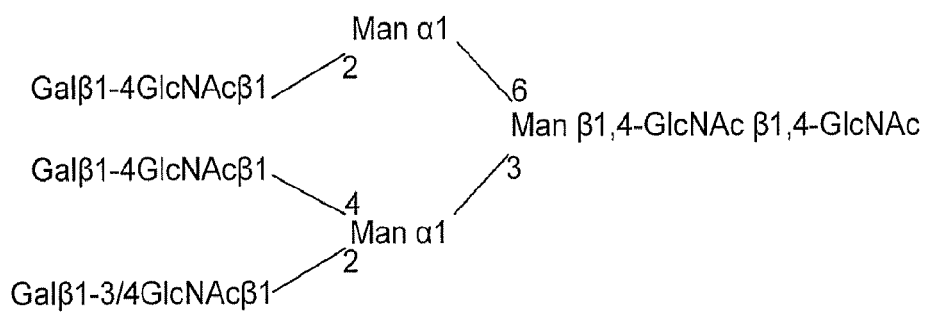
NA3 N-linked oligosaccharide    FIG. 4C

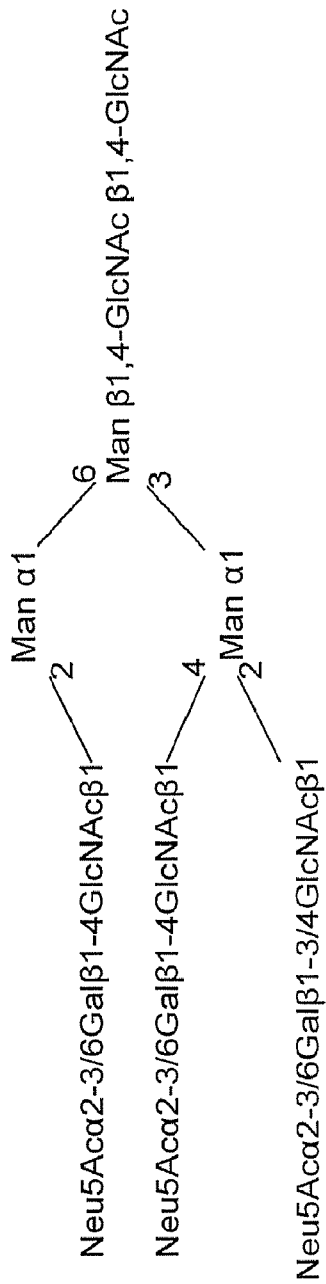
A3 N-linked oligosaccharide  FIG. 4D
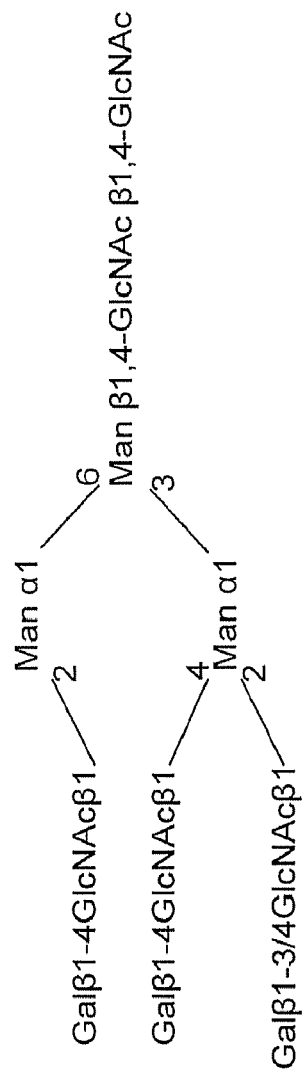
NA3 N-linked oligosaccharide  FIG. 4E

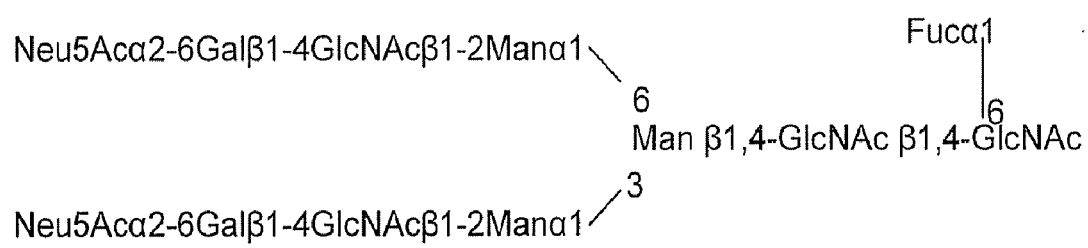
A2F N-linked oligosaccharide    FIG. 4F
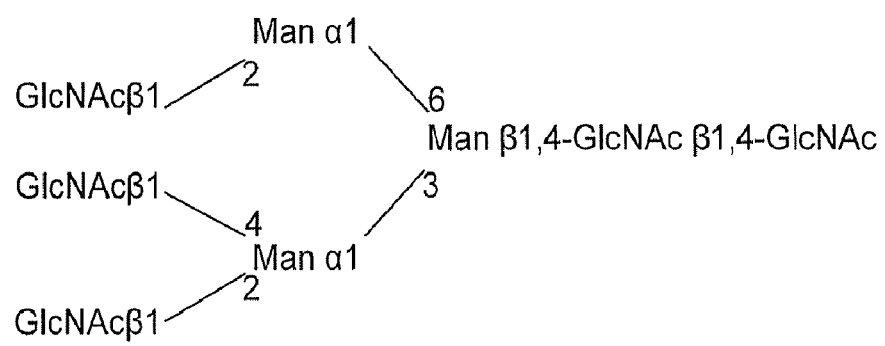
NGA3 N-linked oligosaccharide    FIG. 4G

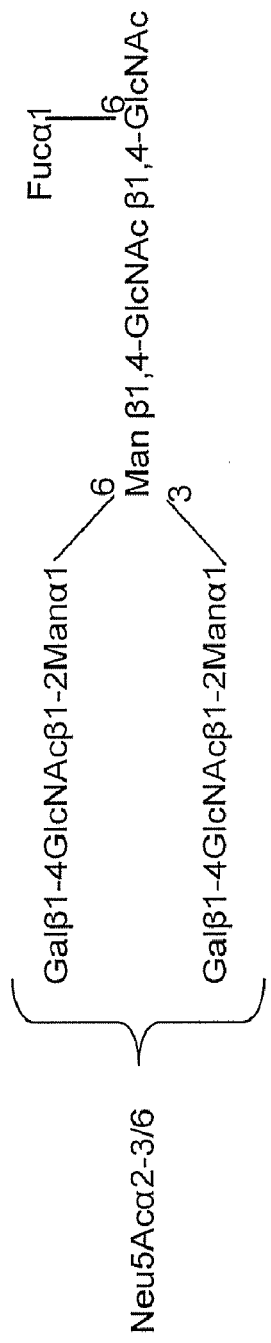
FIG. 4H A1F N-linked oligosaccharide
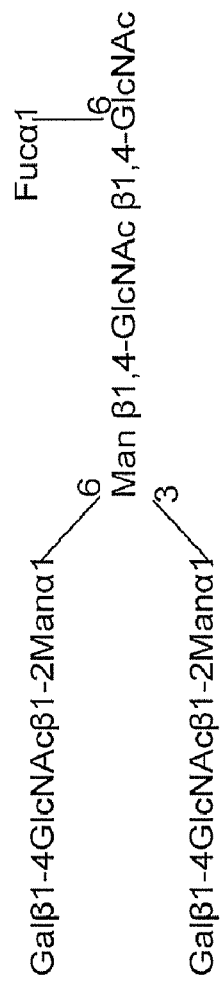
FIG. 4I NA2F N-linked oligosaccharide

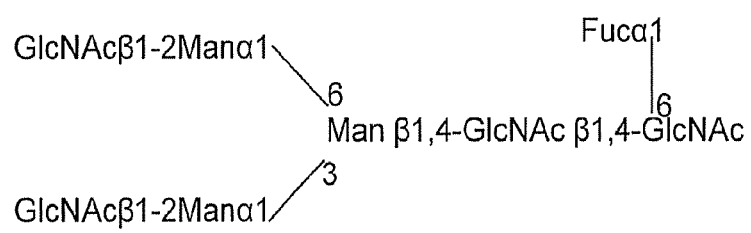
NGA2F N-linked oligosaccharide     FIG. 4J
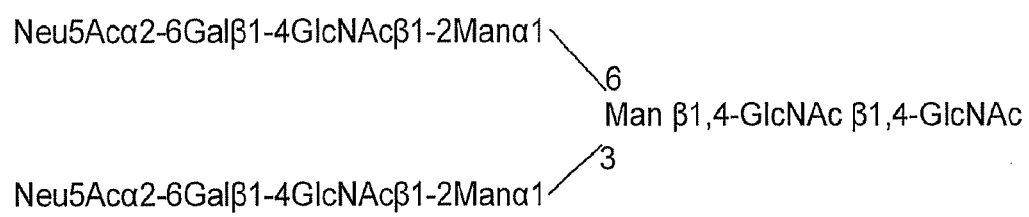
A2 N-linked oligosaccharide     FIG. 4K

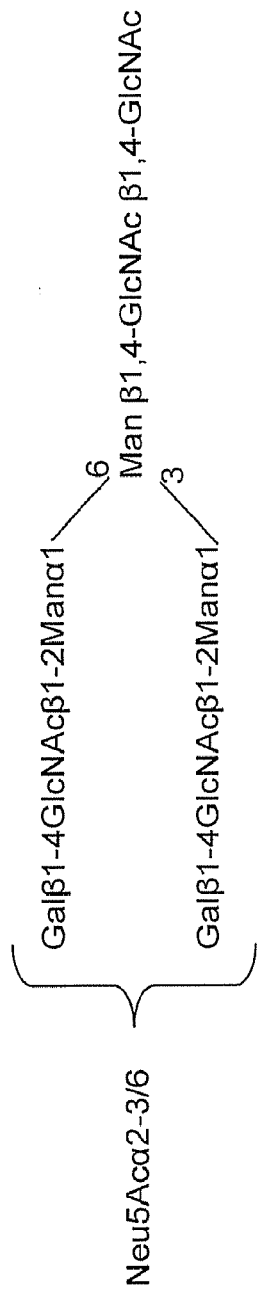
FIG. 4L  A1 N-linked oligosaccharide
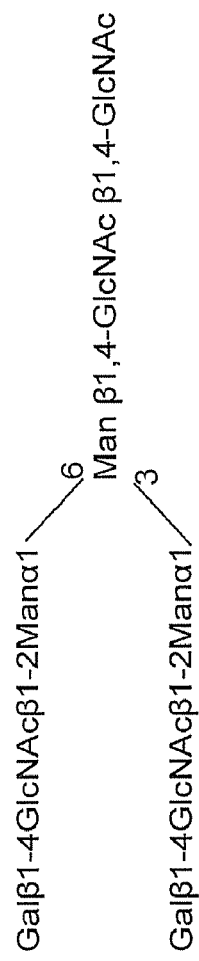
FIG. 4M  NA2 N-linked oligosaccharide

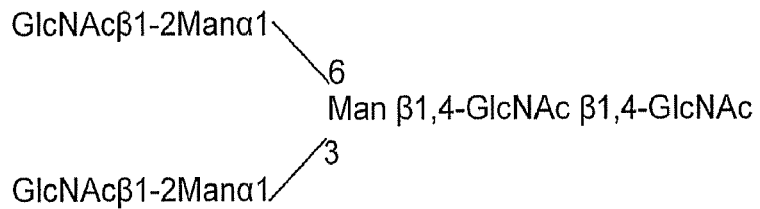
NGA2 N-linked oligosaccharide    FIG. 4N
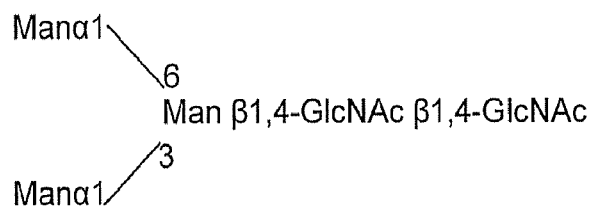
M3N2 N-linked oligosaccharide    FIG. 4O
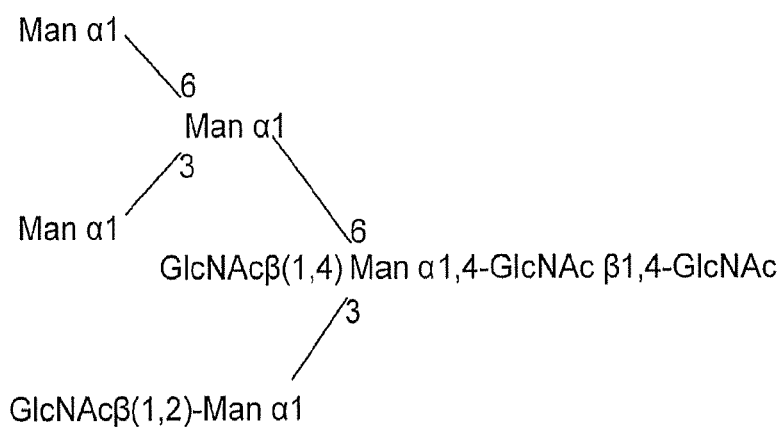
Hybrid N-linked oligosaccharide    FIG. 4P

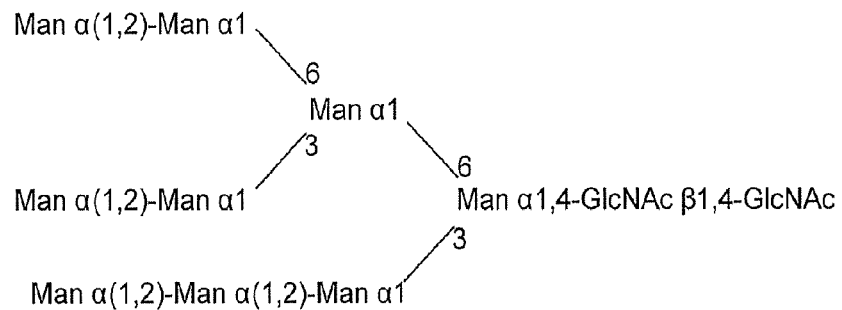
Man-9 N-linked oligosaccharide    FIG. 4Q
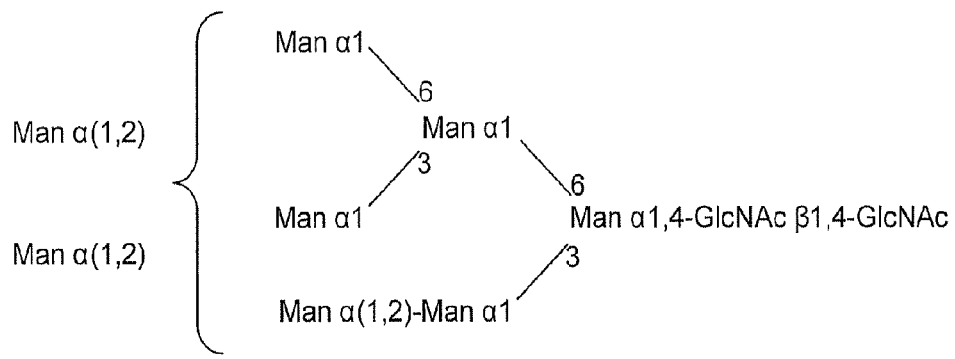
Man-8 N-linked oligosaccharide    FIG. 4R
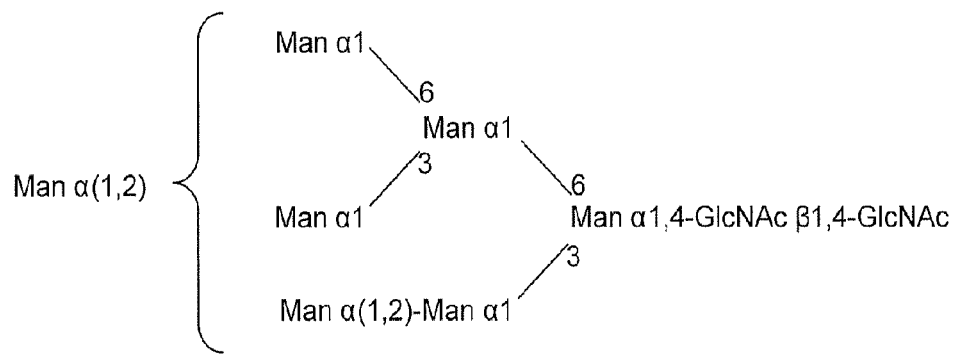
Man-7 N-linked oligosaccharide    FIG. 4S

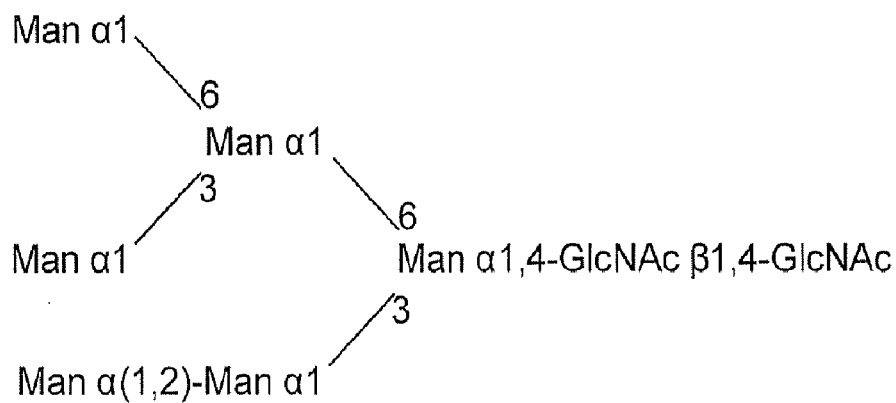
Man-6 N-linked oligosaccharide     FIG. 4T
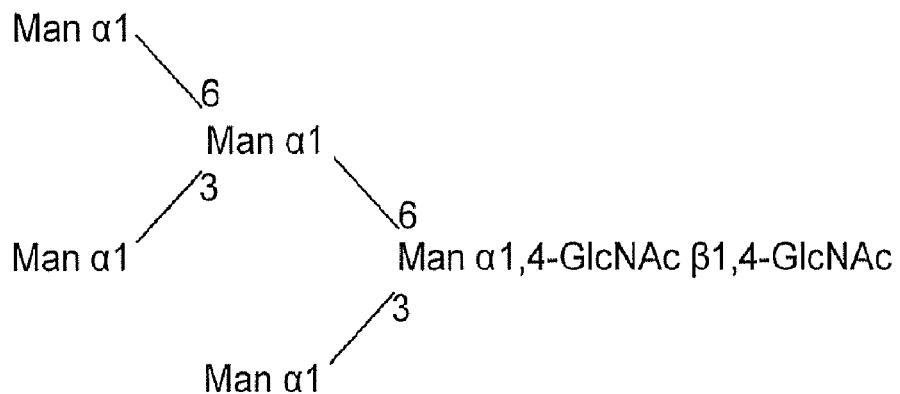
Man-5 N-linked oligosaccharide     FIG. 4U

CHEMICAL SHIFTS

| Residue | Linkage | Fig 12 (Unlabeled) | | Fig 14 (2AB-labeled) | |
|---|---|---|---|---|---|
| | | 1H | 13C | 1H | 13C |
| mannose-4 | mono-antennary | 5.10-5.15 | 102.2-102.6 | 5.10-5.15 | 101.7-102.7 |
| mannose-4 | bi-antennary | 5.10-5.15 | 101.7-102.1 | 5.10-5.15 | 101.5-102.5 |
| mannose-4' | mono-antennary | 4.90-4.95 | 98.8-99.8 | 4.90-4.95 | 99.5-100.5 |
| mannose-4' | bi-antennary | 4.83-4.88 | 99.5-100.5 | 4.83-4.88 | 99.5-100.5 |
| GlcNAc1α | ? | 5.15-5.20 | 93-94 | ? | ? |
| GlcNAc1β | ? | 4.65-4.70 | 97-98 | ? | ? |
| GlcNAc2 | ? | 4.63-4.68 | 103.5-104.5 | 4.68-4.73 | 103.3-104.3 |
| mannose-3 | ? | 4.72-4.77 | 102.7-103.7 | 4.72-4.77 | 102.7-103.7 |
| GlcNAc | β(1-2) linkage to mannose | 4.55-4.60 | 102-103 | 4.55-4.60 | 102-103 |
| GlcNAc | β(1-4) or β(1-6) linkage to mannose | 4.52-4.58 | 104-105 | 4.52-4.57 | 104-105 |
| GlcNAc | lactosamine extension | 4.67-4.72 | 105-106 | 4.67-4.72 | 105-106 |

FIG. 16

| Residue | Linkage | CHEMICAL SHIFTS | | | |
|---|---|---|---|---|---|
| | | Fig 12 (Unlabeled) | | Fig 14 (2AB-labeled) | |
| | | 1H | 13C | 1H | 13C |
| galactose | unsubstituted (no sialic acid) | 4.43-4.48 | 105-106 | 4.43-4.48 | 105-106 |
| galactose | α(2-3) sialic acid attached | 4.52-4.57 | 105-106 | 4.52-4.57 | 105-106 |
| galactose | lactosamine extension | 4.52-4.57 | 105-106 | 4.52-4.57 | 105-106 |
| mannose | high-mannose spp. | 5.35-5.45; 5.05-5.15; 4.95-5.05 | 103-104; 104.5-105.5; 105-106 | 5.35-5.45; 5.05-5.15; 4.95-5.05 | 103-104; 104.5-105.5; 102.7-103.7 |
| core fucose | ~ | 4.87-4.93 | 101.7-102.7 | 4.88-4.93; 4.82-4.88 | 101-102; 101-102 |

FIG. 16 Cont'd

| Residue | Linkage | CHEMICAL SHIFTS | | | |
|---|---|---|---|---|---|
| | | Fig 12 (Unlabeled) | | Fig 14 (2AB-labeled) | |
| | | 1H | 13C | 1H | 13C |
| mannose-4 | mono-antennary | 5.10-5.15 | 102.2-102.6 | 5.10-5.15 | 101.7-102.7 |
| mannose-4 | bi-antennary | 5.10-5.15 | 101.7-102.1 | 5.10-5.15 | 101.5-102.5 |
| mannose-4' | mono-antennary | 4.90-4.95 | 98.8-99.8 | 4.90-4.95 | 99.5-100.5 |
| mannose-4' | bi-antennary | 4.83-4.88 | 99.5-100.5 | 4.83-4.88 | 99.5-100.5 |
| GlcNAc1α | ? | 5.15-5.20 | 93-94 | ? | ? |
| GlcNAc1β | ? | 4.65-4.70 | 97-98 | ? | ? |
| GlcNAc2 | ? | 4.63-4.68 | 103.5-104.5 | 4.68-4.73 | 103.3-104.3 |
| mannose-3 | ? | 4.72-4.77 | 102.7-103.7 | 4.72-4.77 | 102.7-103.7 |
| GlcNAc | β(1-2) linkage to mannose | 4.55 - 4.60 | 102-103 | 4.55-4.60 | 102-103 |
| GlcNAc | β(1-4) or β(1-6) linkage to mannose | 4.52 - 4.58 | 104-105 | 4.52-4.57 | 104-105 |
| GlcNAc | lactosamine extension | 4.67-4.72 | 105-106 | 4.67-4.72 | 105-106 |

FIG. 16A

| Residue | Linkage | CHEMICAL SHIFTS | | | |
|---|---|---|---|---|---|
| | | Fig 12 (Unlabeled) | | Fig 14 (2AB-labeled) | |
| | | 1H | 13C | 1H | 13C |
| galactose | unsubstituted (no sialic acid) | 4.43-4.48 | 105-106 | 4.43-4.48 | 105-106 |
| galactose | α(2-3) sialic acid attached | 4.52-4.57 | 105-106 | 4.52-4.57 | 105-106 |
| galactose | lactosamine extension | 4.52-4.57 | 105-106 | 4.52-4.57 | 105-106 |
| mannose | high-mannose spp. | 5.35-5.45; 5.05-5.15; 4.95-5.05 | 103-104; 104.5-105.5; 105-106 | 5.35-5.45; 5.05-5.15; 4.95-5.05 | 103-104; 104.5-105.5; 102.7-103.7 |
| core fucose | ~ | 4.87-4.93 | 101.7-102.7 | 4.88-4.93; 4.82-4.88 | 101-102; 101-102 |

FIG. 16B

CHARACTERIZATION OF N-GLYCAN MIXTURES BY NUCLEAR MAGNETIC RESONANCE

CROSS-REFERENCE TO RELATED APPLICATIONS

This application claims the benefit under 35 U.S.C. 371 of International Application Number PCT/US08/60328 (published on Oct. 23, 2008, as PCT publication number WO/2008/128218), filed Apr. 15, 2008 ("the '328 application"), which claims priority under 35 U.S.C. §119(e) to U.S. provisional application Ser. No. 60/923,686, filed Apr. 16, 2007, the entire contents of all of which are incorporated herein by reference.

BACKGROUND

Many drugs in use today are "small molecule drugs." These drugs exist as simple chemical structures that are synthetically derived. The active ingredient generally exists as a homogenous product. These small molecule drugs and preparations thereof, can be chemically characterized using a variety of analytical tools and are generally readily manufactured through comparatively simple chemical synthesis.

A typical glycoprotein product differs substantially in terms of complexity from a typical small molecule drug. In particular, the sugar structures attached to the amino acid backbone of a glycoprotein can vary structurally in many ways including, sequence, branching, sugar content, and heterogeneity. Thus, glycoprotein products can be complex heterogeneous mixtures of many structurally diverse molecules which themselves have complex glycan structures. N-linked glycans are an important class of branched sugars found in glycoproteins which have a conserved core structure with variations in branching and substitutions of the sugar residues. Glycosylation adds not only to the molecules structural complexity but affects or conditions many of a glycoprotein's biological and clinical attributes.

To date, the creation of glycoprotein drugs having defined properties, whether an attempt to produce a generic version of an existing drug or to produce a second generation or other glycoprotein having improved or desirable properties has been challenging due to the difficulty in synthesizing and characterizing these complex chemical structures and mixtures that contain them.

The situation with regard to the production of generic products is indicative of the problems faced in making glycoprotein drugs having defined properties. While abbreviated regulatory procedures have been implemented for generic versions of small molecule drug products, many in the biotechnology and pharmaceutical industry have taken the view that the complexity of glycoprotein drug products makes them unsuitable for similar approaches.

There is therefore a need in the art for methods for characterizing glycoproteins. In particular, there is a need for analytical methods that are capable of characterizing complex mixtures of glycans, e.g., mixtures obtained by cleaving a plurality of N-glycans from a glycoprotein preparation.

SUMMARY

The present disclosure provides nuclear magnetic resonance (NMR) methods for characterizing mixtures of N-linked glycans. In general, NMR has difficulty analyzing mixtures of different molecules because it is very difficult, often impossible, to tell which signals in an NMR spectrum come from which molecules. This is particularly true when the mixture includes complex molecules and especially if they share common chemical structures, e.g., a mixture of N-glycans. Indeed, NMR spectra of glycans are highly complex and heavily overlapping with most $^1$H signals occurring within the chemical shift range of 3.5-5.5 ppm. Unexpectedly, we have been able to show that subtle differences in glycan structures can give rise to signal shifts which can be resolved and therefore quantified by two dimensional (or in some cases one dimensional) NMR experiments. The present disclosure therefore solves the aforementioned challenges in part by identifying NMR signals that can be resolved in spectra of glycan mixtures and that are diagnostic of particular glycan structural features. Without limitation, methods of the present disclosure may be useful in characterizing monosaccharide composition, branching, fucosylation, sulfation, phosphorylation, sialylation linkages, presence of impurities and/or efficiency of a labeling procedure (e.g., labeling with a fluorophore such as 2-AB). In certain embodiments, the methods can be used quantitatively. In certain embodiments, the methods can be combined with enzymatic digestion to further characterize glycan mixtures.

DEFINITIONS

Approximately, About, Ca.: As used herein, the terms "approximately", "about" or "ca.," as applied to one or more values of interest, refer to a value that is similar to a stated reference value. In certain embodiments, the terms "approximately", "about" or "ca.," refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Biological sample: The term "biological sample", as used herein, refers to any solid or fluid sample obtained from, excreted by or secreted by any living cell or organism, including, but not limited to, tissue culture, bioreactors, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

Cell-surface glycoprotein: As used herein, the term "cell-surface glycoprotein" refers to a glycoprotein, at least a portion of which is present on the exterior surface of a cell. In some embodiments, a cell-surface glycoprotein is a protein that is positioned on the cell-surface such that at least one of the glycan structures is present on the exterior surface of the cell.

Cell-surface glycan: A "cell-surface glycan" is a glycan that is present on the exterior surface of a cell. In many embodiments, a cell-surface glycan is covalently linked to a polypeptide as part of a cell-surface glycoprotein. A cell-surface glycan can also be linked to a cell membrane lipid.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'-sulfo N-acetylglucosamine, etc). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycan preparation: The term "glycan preparation" as used herein refers to a set of glycans obtained according to a particular production method. In some embodiments, glycan preparation refers to a set of glycans obtained from a glycoprotein preparation (see definition of glycoprotein preparation below).

Glycoconjugate: The term "glycoconjugate", as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc.

Glycoform: The term "glycoform", is used herein to refer to a particular form of a glycoconjugate. That is, when the same backbone moiety (e.g., polypeptide, lipid, etc) that is part of a glycoconjugate has the potential to be linked to different glycans or sets of glycans, then each different version of the glycoconjugate (i.e., where the backbone is linked to a particular set of glycans) is referred to as a "glycoform".

Glycolipid: The term "glycolipid" as used herein refers to a lipid that contains one or more covalently linked sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may be comprised of one or more branched chains. In certain embodiments, sugar moieties may include sulfate and/or phosphate groups. In certain embodiments, glycoproteins contain O-linked sugar moieties; in certain embodiments, glycoproteins contain N-linked sugar moieties.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods of the present disclosure comprise cleaving a cell surface glycoprotein with a protease to liberate the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments (e.g., glycopeptides) of cell surface glycoproteins, cell surface glycans attached to cell surface glycoproteins, peptide backbones of cell surface glycoproteins, fragments of such glycoproteins, glycans and/or peptide backbones, and combinations thereof.

Glycosidase: The term "glycosidase" as used herein refers to an agent that cleaves a covalent bond between sequential sugars in a glycan or between the sugar and the backbone moiety (e.g. between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent.

Glycosylation pattern: As used herein, the term "glycosylation pattern" refers to the set of glycan structures present on a particular sample. For example, a particular glycoconjugate (e.g., glycoprotein) or set of glycoconjugates (e.g., set of glycoproteins) will have a glycosylation pattern. In some embodiments, reference is made to the glycosylation pattern of cell-surface glycans. A glycosylation pattern can be characterized by, for example, the identities of glycans, amounts (absolute or relative) of individual glycans or glycans of particular types, degree of occupancy of glycosylation sites, etc., or combinations of such parameters.

Glycoprotein preparation: A "glycoprotein preparation", as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms.

N-glycan: The term "N-glycan", as used herein, refers to a polymer of sugars that has been released from a glycoconjugate but was formerly linked to the glycoconjugate via a nitrogen linkage (see definition of N-linked glycan below).

N-linked glycans: N-linked glycans are glycans that are linked to a glycoconjugate via a nitrogen linkage. A diverse assortment of N-linked glycans exists, but is typically based on the common core pentasaccharide $(Man)_3(GlcNAc)(GlcNAc)$.

O-glycan: The term "O-glycan", as used herein, refers to a polymer of sugars that has been released from a glycoconjugate but was formerly linked to the glycoconjugate via an oxygen linkage (see definition of O-linked glycan below).

O-linked glycans: O-linked glycans are glycans that are linked to a glycoconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L-serine (Ser) or L-threonine (Thr). Some O-linked glycans also have modifications such as acetylation and sulfation. In some instances O-linked glycans are attached to glycoproteins via fucose or mannose to the hydroxyl group of L-serine (Ser) or L-threonine (Thr).

Phosphorylation: As used herein, the term "phosphorylation" refers to the process of covalently adding one or more phosphate groups to a molecule (e.g., to a glycan).

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Sialic acid: The term "sialic acid", as used herein, is a generic term for the N- or O-substituted derivatives of neuraminic acid, a nine-carbon monosaccharide. The amino group of neuraminic acid typically bears either an acetyl or a glycolyl group in a sialic acid. The hydroxyl substituents present on the sialic acid may be modified by acetylation, methylation, sulfation, and phosphorylation. The predominant sialic acid is N-acetylneuraminic acid (Neu5Ac). Sialic acids impart a negative charge to glycans, because the carboxyl group tends to dissociate a proton at physiological pH. Exemplary deprotonated sialic acids are as follows:

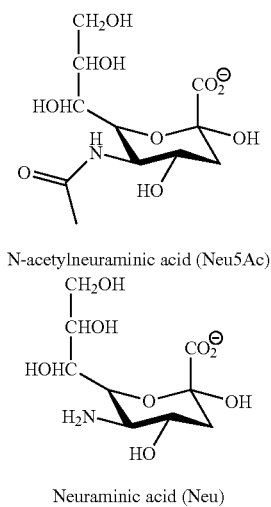

N-acetylneuraminic acid (Neu5Ac)

Neuraminic acid (Neu)

Signal integral: As used herein, the terms "signal integral" refer to the magnitude of a particular signal (including cross-peaks) within an NMR spectrum. In one embodiment, the signal integral is obtained by measuring the signal area (for peaks in a one dimensional spectrum) or signal volume (for cross-peaks in a multi-dimensional spectrum). In one embodiment, the signal integral is obtained by measuring the signal intensity.

BRIEF DESCRIPTION OF THE DRAWING

FIGS. 4A-4U shows the structures of exemplary N-glycans.

DETAILED DESCRIPTION OF CERTAIN EMBODIMENTS

Figure 1:
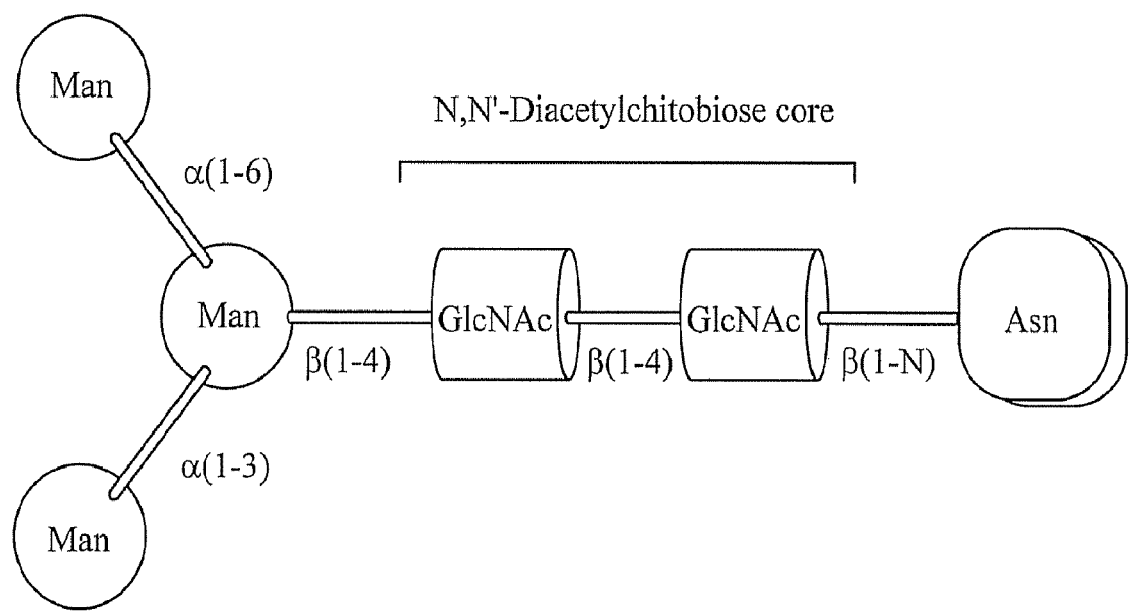
FIG. 1 shows the structure of the common core pentasaccharide $(Man)_3(GlcNAc)(GlcNAc)$ of N-glycans.
Figure 2:
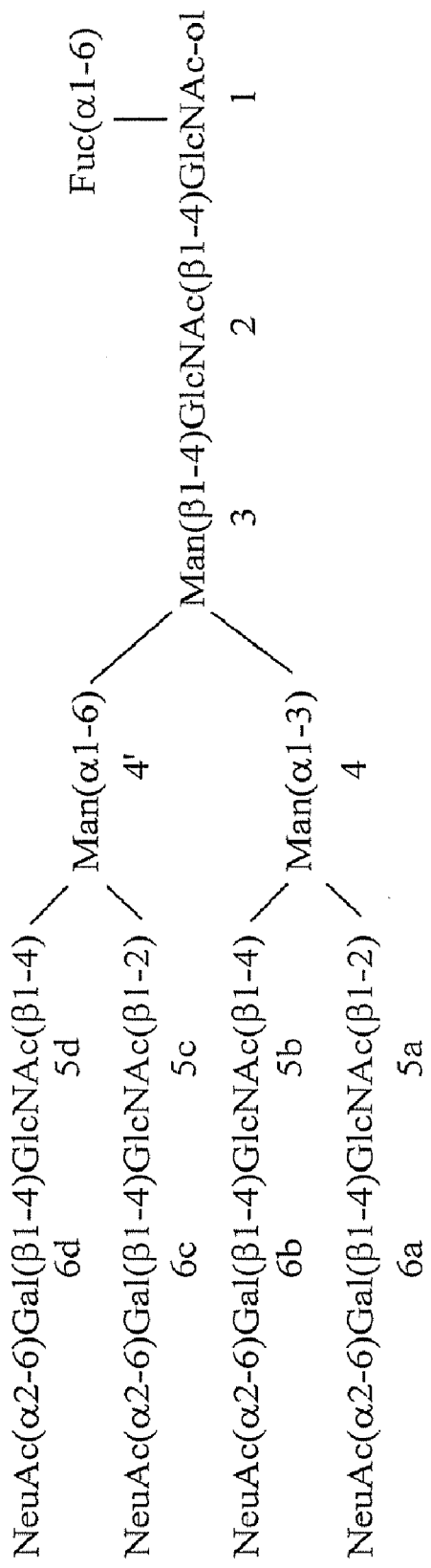
FIG. 2 shows the structure of an exemplary tetrasialo tetraantennary fucosylated N-glycan. The numbering scheme used to identify the residues throughout the text is shown.

N-linked glycans are glycans that are linked to a glycoconjugate via a nitrogen linkage. The diverse assortment of N-glycans are based on the common core pentasaccharide $(Man)_3(GlcNAc)(GlcNAc)$ (see FIG. 1). An exemplary tetraantennary N-glycan is shown in FIG. 2. Typical N-glycans may vary in the fucosylation of GlcNAc1, the number of branches of the Man4 and 4' residues, and the sialylation of the branches. Additionally, the sugar residues may be modified, such as by sulfation or phosphorylation. Extensions of the branches are possible by the insertion of a lactosamine.

Figure 3B:
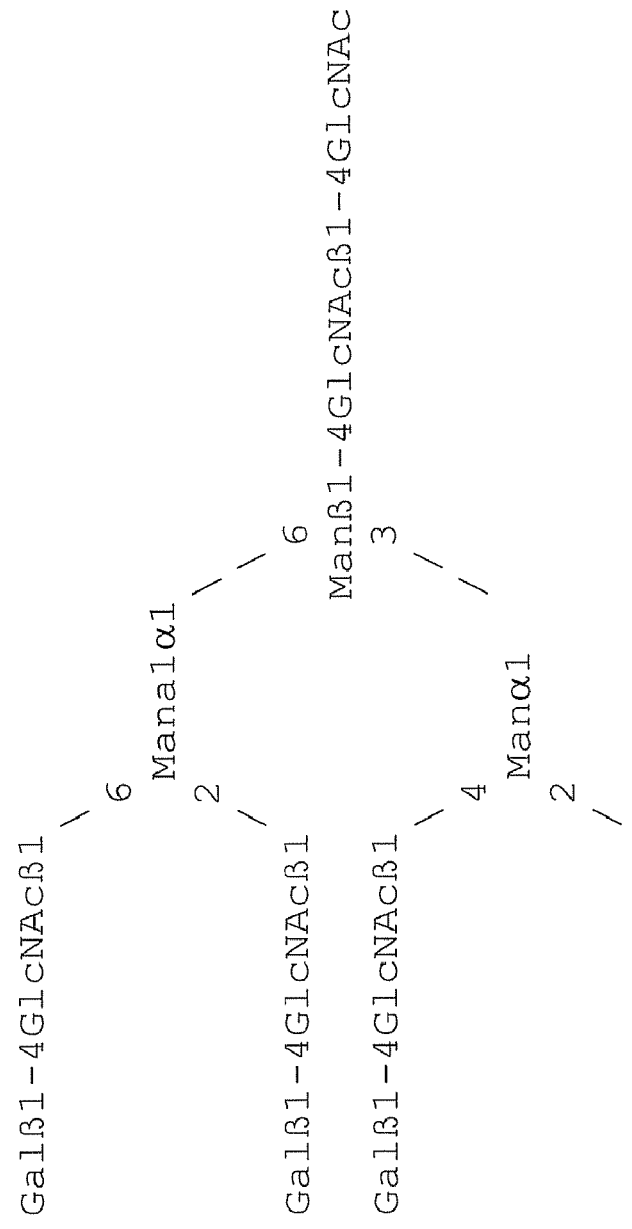
FIG. 3 shows the structures of the standard N-glycans (a) A1F, (b) NA3 and (c) NA4.

For illustrative purposes, FIG. 3 shows the structures of three different model N-glycans, namely A1F which is a monosialo ($\alpha$2-6) biantennary fucosylated N-glycan, NA3 which is an asialo triantennary N-glycan in which the Man4' is monosubstituted, and NA4 which is an asialo tetraantennary N-glycan. The structures of these and other exemplary N-glycans are compared in FIGS. 4A to 4U. In general, N-glycans may be grouped as "complex" A-4 (tetraantennary, such as NA4 and NGA4); A-3 (triantennary, such as A3, NA3, NGA3); A2F (fucosylated and biantennary, such as A2F, A1F, NA2F, NGA2F); A-2 (biantenarry, such as A2); "hybrid" and "high mannose" (e.g., Man-5, Man-6, Man-7, Man-8, Man-9) type.

N-linked glycans are commonly found as components of proteins (i.e., a glycoprotein). N-linked glycans are linked to the glycoprotein in the endoplasmic reticulum and the Golgi apparatus via a N-linkage. Typically, glycans are added to the glycoprotein in the lumen of the endoplasmic reticulum. The glycan is added to the amino group on the side chain of an asparagine residue contained within the target consensus sequence of Asn-X-Ser/Thr, where X may be any amino acid except proline, to provide an N-linked glycan. The initial glycan chain is usually trimmed by specific glycosidase enzymes in the endoplasmic reticulum, resulting in a short, branched core comprised of two N-acetylglucosamine and three mannose residues. After initial processing in the endoplasmic reticulum, the glycoprotein is then transported to the Golgi where further processing may take place. The trimmed N-linked glycan moiety may be modified by the addition of several mannose residues, resulting in a 'high-mannose oligosaccharide'. Additionally or alternatively, one or more monosaccharides units of N-acetylglucosamine may be added to the core mannose subunits to form 'complex glycans'. Galactose may be added to the N-acetylglucosamine subunits, and sialic acid subunits may be added to the galactose subunits, resulting in a chain that terminates with any of a sialic acid, a galactose or an N-acetylglucosamine residue. Additionally, a fucose residue may be added to an N-acetylglucosamine residue of the glycan core. Each of these additions is catalyzed by specific glycosyl transferases.

As described below, we have used the model N-glycans of FIG. 3 and mixtures of N-glycans to identify features in different types of NMR spectra that can be used to characterize various aspects of N-glycans. In particular, we have identified NMR signals with chemical shifts that are diagnostic of glycan structural features and that can be resolved in spectra of certain glycan mixtures.

The following sections describe particular 1D $^1$H, 2D $^1$H-$^1$H and 2D $^1$H-$^{13}$C experiments that were used to identify diagnostic NMR signals. It is to be understood that the methods are in no way limited to the specific pulse sequences or experiments described herein. Thus, any NMR pulse sequence or experiment that is capable of identifying a $^1$H chemical shift, $^1$H-$^1$H scalar correlation, $^1$H-$^{13}$C scalar correlation or other NMR signal that is described herein may be used in a method. In general, it will be appreciated that the choice of experiment may depend on factors such as the specific chemical shift(s) of interest, spectral crowding, amount and nature of sample, desired timeframe, need for quantitative information, etc. It will also be appreciated that the methods are in no way limited to the specific chemical shifts described herein. In particular, it is well known that chemical shifts may vary depending on experimental conditions, e.g., solvent, temperature, etc. Thus, whenever we refer to a particular chemical shift herein it is to be understood that this is in reference to a particular set of experimental conditions. Those skilled in the art will be able to determine suitable chemical shifts for NMR signals described herein under different experimental conditions.

$^1$H Chemical Shifts

In one aspect, the present disclosure provides methods which utilize $^1$H chemical shifts to identify a structural characteristic of N-glycans. While these $^1$H chemical shifts may be obtained from a simple 1D $^1$H NMR spectrum, they may also be obtained from a 2D $^1$H-$^1$H spectrum, a 2D $^1$H-$^{13}$C spectrum, etc. According to this aspect of the disclosure, a sample is provided which includes a mixture of N-glycans. $^1$H chemical shifts in the sample are then obtained according to any method known in the art. In the Examples we describe the use of 1D $^1$H NMR spectra that were obtained on a 600 MHz Bruker Avance spectrometer with 5 mm cryoprobe at 27° C. with presaturation of the water resonance. Each spectrum was obtained by averaging 16 to 256 scans. The recycle delay was 14 s. It will be appreciated however that for purposes of this disclosure, the 1D $^1$H spectra may be obtained using higher or lower field spectrometers, using different probes, conditions, water suppression sequence, recycle delay, detector cycling, etc.

We have found that despite the significant spectral crowding in 1D $^1$H spectra, these spectra can provide quantitative information even on complex mixtures of N-glycans in $D_2O$. For purposes of illustration, 1D spectra of the three model N-glycans of FIG. 3 and of a mixture of N-glycans are shown in FIGS. 5*a*-5*c* and 5*d*, respectively. The $^1$H chemical shifts in these spectra provide much structural information. Thus once the $^1$H chemical shifts have been obtained (e.g., from a 1D $^1$H spectrum), the methods include a step of identifying whether the $^1$H chemical shifts includes one or more shifts that are associated with a structural characteristic. The outcome of this identification step is then used to determine whether the sample includes a glycan with the structural characteristic.

In some embodiments, the specific chemical shift is within the anomeric region (ca. 4.5 ppm to ca. 5.5 ppm) which is the most resolved region of the 1D $^1$H spectrum (although the residual water signal at ca. 4.8 ppm partially obscures some of the anomeric signals). For example, we have found that the presence of oligomannose structures can be detected by analysis of the anomeric region. Oligomannose residues present characteristic and well resolved anomeric signals at ca. 5.00-5.10 ppm and ca. 5.35-5.45 ppm, as shown with an asterisk (*) in FIG. 6. Additional characteristic signals are described herein.

In some embodiments, the specific signal or signals are in the methyl region (ca. 0.7 ppm to ca. 2.8 ppm). For example, in one embodiment, the methods involve determining whether the spectrum includes a chemical shift at ca. 2.0 ppm which belongs to the acetyl methyl-$^1$H signal of GlcNAc or a sialic acid. In certain embodiments, GlcNAc and sialic acids can be distinguished on the basis of the axial and equatorial H3 signals of sialic acids that are readily observed in the range of ca. 1.6 ppm to ca. 1.9 ppm and ca. 2.6 ppm to ca. 2.8 ppm, respectively (see FIGS. 5a and d). In some embodiments, the sialic acid H3 axial signal can be used as a diagnostic of the linkage type, with α2-3 and α2-6 linkages resonating at ca. 1.7 ppm and ca. 1.8 ppm, respectively. As discussed below, a 2D $^1$H-$^1$H TOCSY spectrum can provide additional resolution by the well-resolved H3 axial and H3 equatorial crosspeaks.

Figure 7:
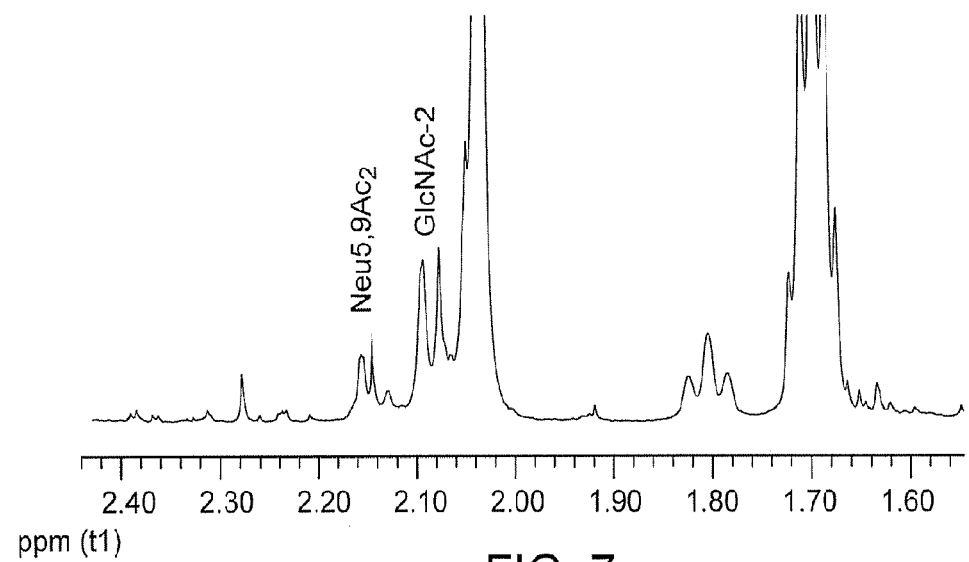
FIG. 7 shows part of the 1D $^1H$ spectrum of a mixture of N-glycans acquired on a 600 MHz Bruker Avance spectrometer with 5 mm cryoprobe, at 25° C., with presaturation of the water resonance.

In certain embodiments, the presence of di- or tri-acetylated NeuAc (e.g., Neu5,9Ac$_2$) can be identified from a characteristic signal at ca. 2.15 ppm, as indicated in FIG. 7 which was obtained with a mixture of N-glycans.

Figure 5A:
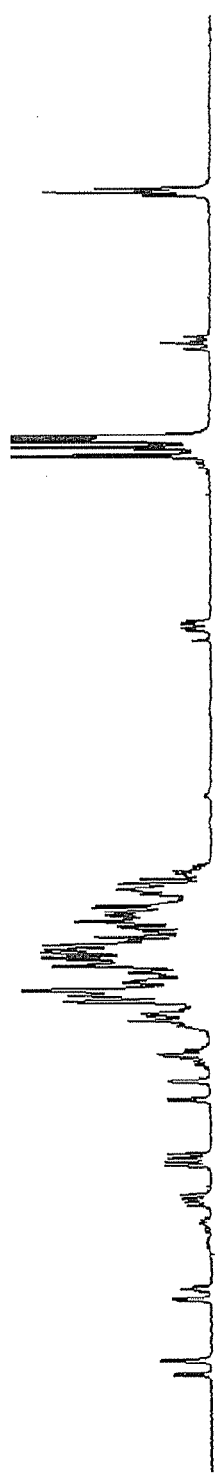
FIG. 5 shows the 1D $^1H$ spectra of (a) A1F, (b) NA3, (c) NA4 and (d) a mixture of N-glycans. The spectra were acquired on a 600 MHz Bruker Avance spectrometer with 5 mm cryoprobe at 27° C. with presaturation of the water resonance. Each spectrum is the average of 16 to 256 scans. The recycle delay was 14 s.
Figure 5B:
Figure 5C:
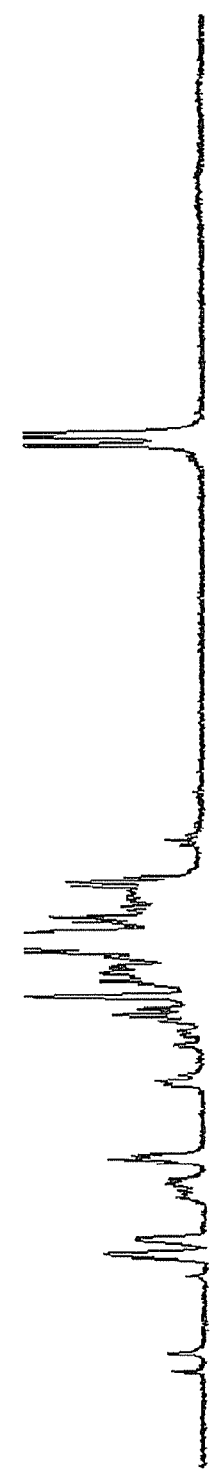
Figure 5D:
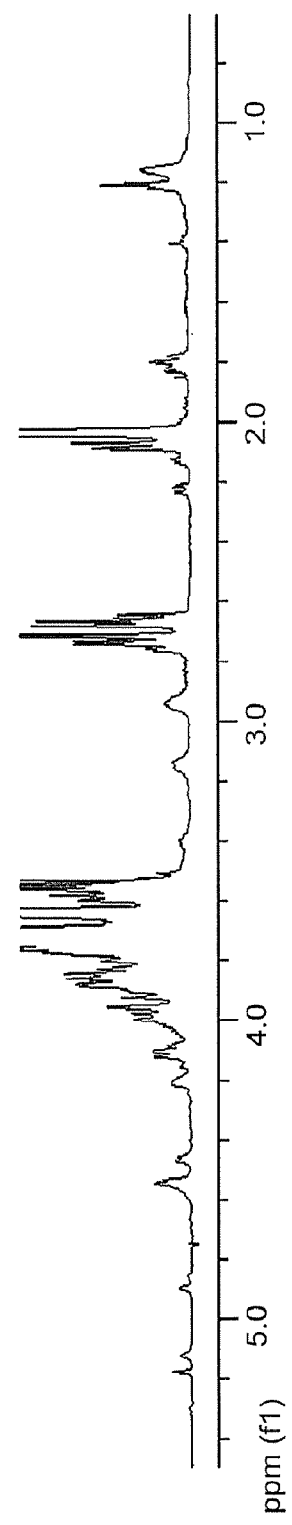
Figure 15:
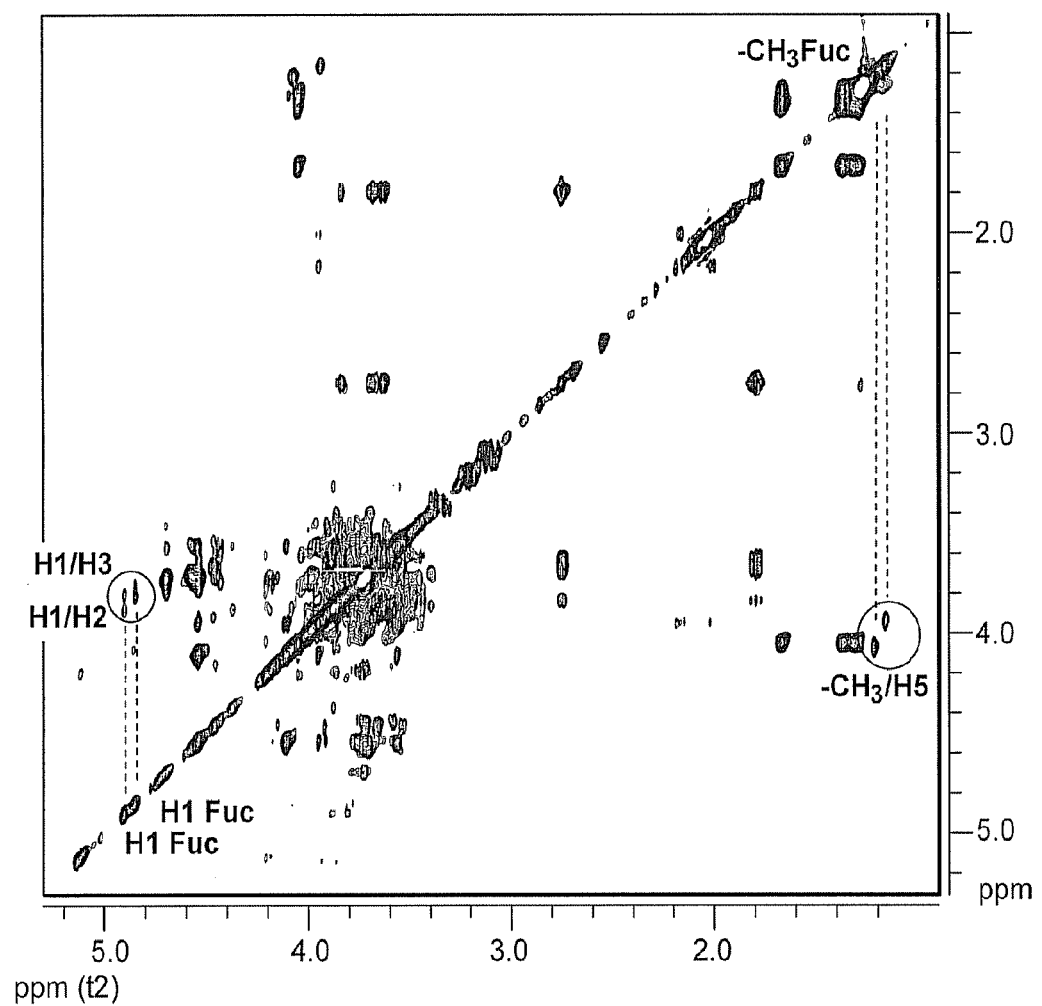
FIG. 15 shows a 2D $^1H$-$^1H$ TOCSY spectrum of a 2AB-labeled N-glycan pool, acquired on a 600 MHz Bruker Avance spectrometer equipped with 5 mm cryoprobe at 25° C. in $D_2O$. Fucose cross-peaks are indicated.

In some embodiments, the presence of fucose within the sample can be determined based on the presence of a methyl-$^1$H signal at ca. 1.2 ppm (see FIGS. 5a and d). As discussed below, the core location of the fucosylation can be confirmed by a $^1$H-$^{13}$C HSQC spectrum (FIG. 11), in which the GlcNAc2 anomeric chemical shift is perturbed by the presence of a fucose on GlcNAc1. As discussed in more detail below and as shown in FIG. 15, we have shown that fucose $^1$H methyl signals can be resolved when fucose occurs in different environments (e.g., in 2AB-labeled and unlabeled glycans). In some embodiments, the sensitivity of the fucose $^1$H methyl signals to their environment can be used to detect and quantify fucose moieties that are in an antennary environment (e.g., as opposed to a core environment). In some embodiments, this is achieved using a 2D $^1$H-$^1$H TOCSY or other homonuclear scalar correlation experiment.

In certain embodiments it may prove advantageous to quantify one or more characteristic $^1$H signals. Each characteristic signal can be quantified by integration. As long as the recycle delay between scans is sufficiently long (typically about five times the longitudinal relaxation time, $T_1$, of the slowest relaxing species), the integrals are quantitative. Signals within ca. 0.2 ppm to ca. 0.3 ppm of the residual water signal (ca. 4.8 ppm) will typically be partially attenuated by the same presaturation used to suppress water and will therefore be less quantitative than those that are further removed. In certain embodiments, peak fitting software may be used to quantify one or more characteristic $^1$H signals. Peak fitting software is particularly useful when two peaks are partially overlapping. In certain embodiments, quantitative results may be used to yield ratios based on comparisons with the results obtained with a different sample (e.g., a calibration standard, a different glycan preparation, etc.).

$^1$H-$^1$H Scalar Correlations

Figure 8:
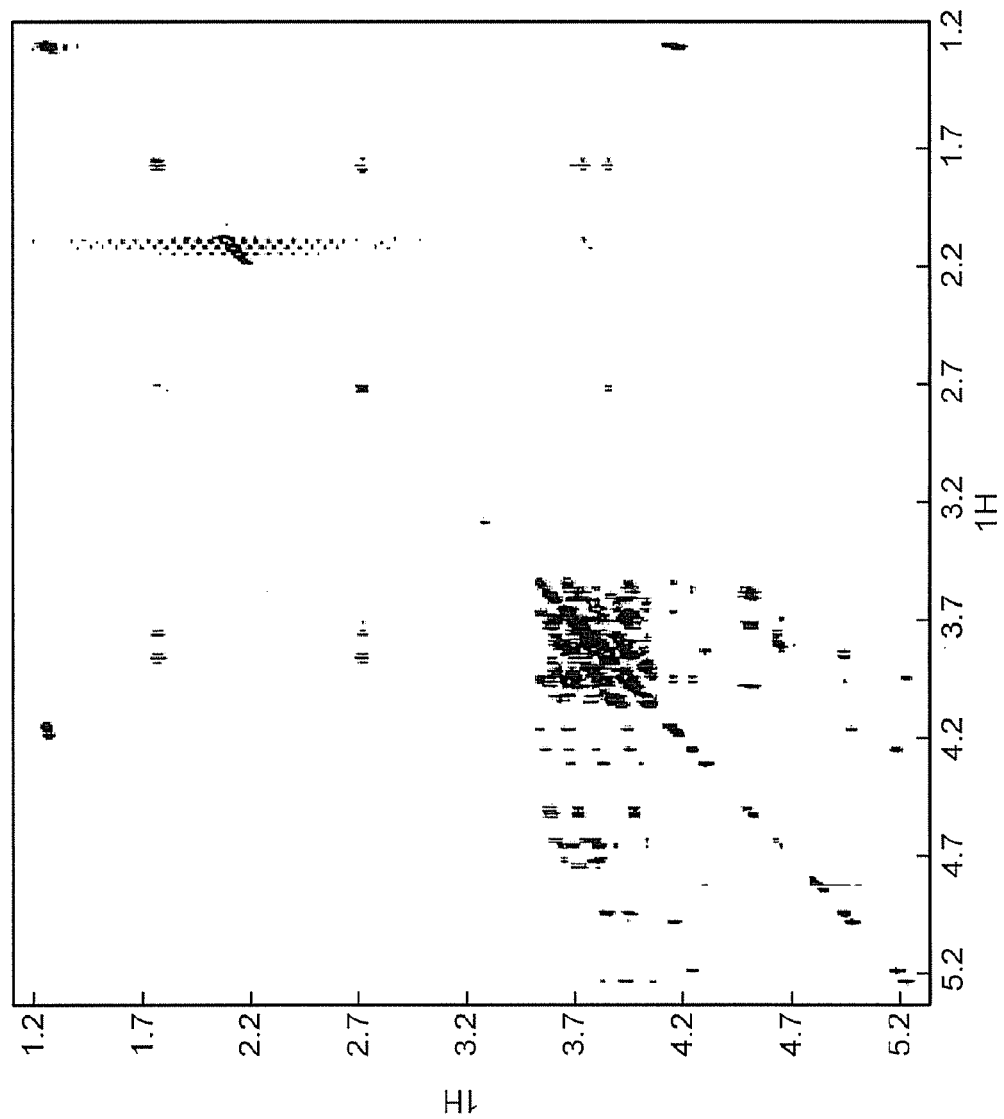
FIG. 8 shows the 2D $^1H$-$^1H$ TOCSY spectrum of A1F. The spectrum was acquired on a 600 MHz Bruker Avance spectrometer with 5 mm cryoprobe at 27° C. using 120 ms MLEV-17 mixing. A total of 4 points were averaged for each of 4096×256 hypercomplex points. The recycle delay was 1.4 s.

In another aspect, structural characteristics of N-glycans can be identified using $^1$H-$^1$H scalar correlations (e.g., without limitation, in a 2D $^1$H-$^1$H TOCSY spectrum). According to this aspect $^1$H-$^1$H scalar correlations are detected for the sample of interest and at least one correlation is identified which is known to be associated with a particular structural characteristic. In the Examples we describe, inter alia, 2D $^1$H-$^1$H TOCSY spectra that were acquired on a 600 MHz Bruker Avance spectrometer with 5 mm cryoprobe at 27° C. using 120 ms MLEV-17 mixing. A total of 4 points were averaged for each of 4096×256 hypercomplex points. The recycle delay was 1.4 s. However, it will be appreciated that the 2D $^1$H-$^1$H TOCSY spectrum may be obtained using any known pulse sequence and any suitable set of experimental conditions. In a 2D $^1$H-$^1$H TOCSY experiment, a 'mixing time' present within the pulse sequence enables magnetization to be transferred using the scalar coupling between protons that are closely linked by chemical bonds. This magnetization transfer results in $^1$H-$^1$H correlations which are nearly always restricted to protons within the same sugar residue. Varying the mixing time used to affect the transfer alters the number of bonds over which the correlations occur. A 2D $^1$H-$^1$H TOCSY spectrum of a model N-glycan (A1F, see FIG. 3) is shown in FIG. 8. In certain embodiments, known $^1$H-$^1$H scalar couplings are used to model the magnetization transfer and thereby adjust any quantitative information obtained from peak integrals. Signals close to the water signal will be partially attenuated by the presaturation used to suppress water.

As described previously, it is to be understood that any NMR experiment may be used to identify $^1$H-$^1$H scalar correlations. Thus, without limitation, instead of a 2D $^1$H-$^1$H TOCSY experiment one could use a 1D $^1$H selective TOCSY experiment, COSY, multiple-quantum-filtered variants of COSY, isotope-filtered versions of COSY and TOCSY, TOCSY-HSQC, TOCSY-HMQC experiments, etc. Useful experiments also include ROESY and NOESY and their variants, insofar as these dipolar-correlation experiments can be utilized to elucidate $^1$H-$^1$H correlations within a monosaccharide ring, and can thereby be utilized to elucidate diagnostic patterns of chemical shifts, pertaining to specific monosaccharide ring structures. Possible experiments also include any selective one dimensional analog of the two dimensional experiments listed above.

As an illustrative example, as mentioned above, while the presence of sialylation can be readily identified from the $^1$H chemical shifts of the axial and equatorial H3 signals, $^1$H-$^1$H scalar correlations provide additional resolution by the location of the well-resolved H3 axial and H3 equatorial crosspeaks, e.g., in a 2D $^1$H-$^1$H TOCSY spectrum (ca. 1.6 ppm to ca. 1.9 ppm/ca. 2.6 ppm to ca. 2.8 ppm).

Figure 9:
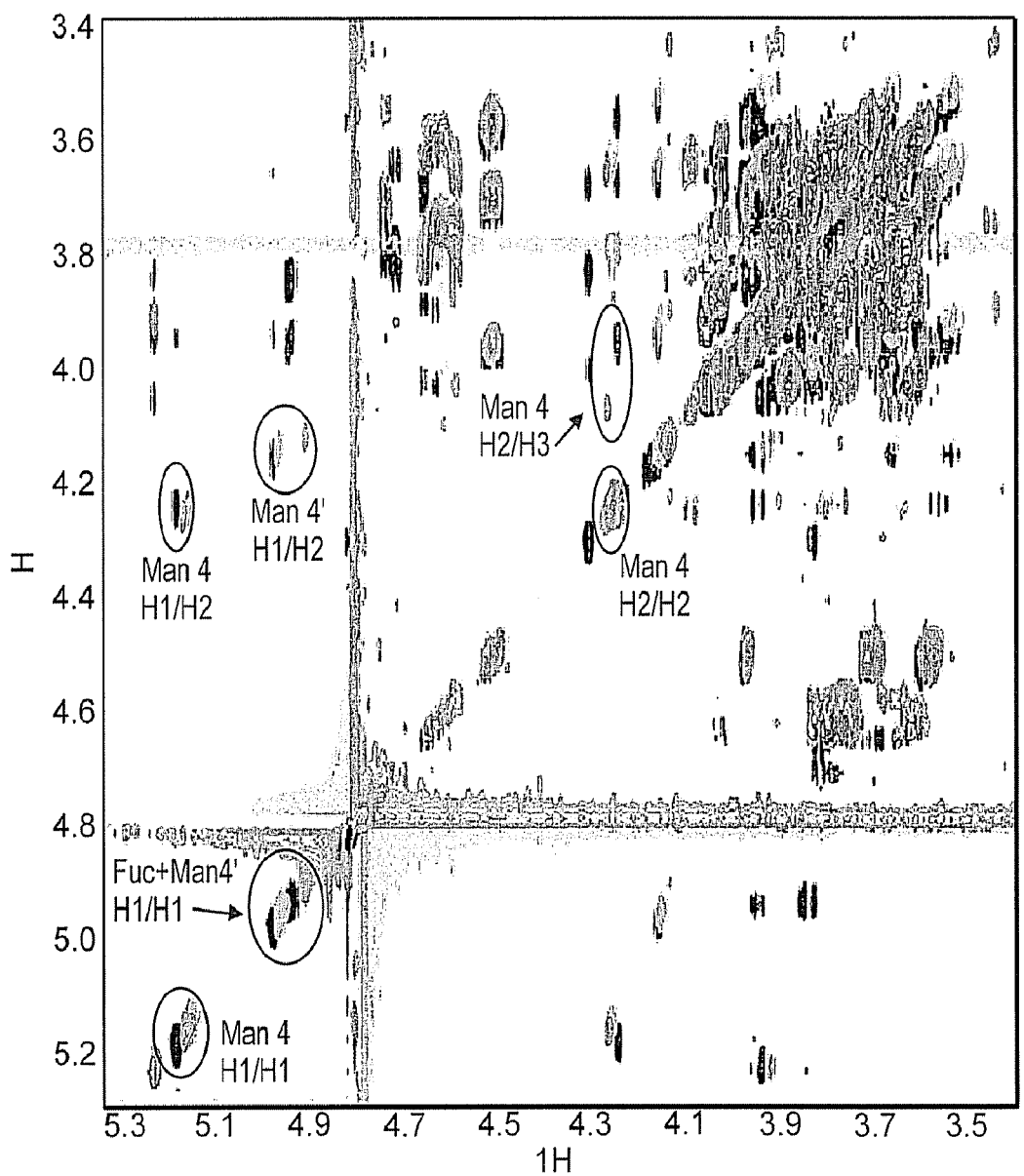
FIG. 9 shows the overlaid 2D $^1H$-$^1H$ TOCSY spectra of the anomeric regions of A1F (black), NA3 (red), and NA4 (green). The H1/H2 cross-peak position of Man4' is diagnostic branching, with the only bisubstituted species, NA4, showing a distinct shift from the others. The H2/H3 cross-peak position of Man4 is diagnostic of branching, with the only monosubstituted species, A1F, showing a distinct shift from the others.

Similarly, $^1$H-$^1$H scalar correlations allows for discrimination between the branching options at the Man4 position as shown in the 2D $^1$H-$^1$H TOCSY spectrum of FIG. 9. The branching of the Man4 residue can be distinguished on the basis of the location of the H2-H3 cross-peak (ca. 4.25 ppm/ ca. 3.90 ppm for mono-antennary vs. ca. 4.25 ppm/ca. 4.10 ppm for bi-antennary).

For example, the chemical shifts of the Man4 cross-peaks may range as follows:
  mono-antennary: H2: ca. 4.2 to 4.3 ppm and H3: ca. 3.85 to ca. 3.95 ppm
  bi-antennary: H2: ca. 4.2 to 4.3 ppm and H3: ca. 4.05 to ca. 4.15 ppm Without limitation, branching at the Man4 position may also be determined by using a 1D $^1$H selective TOCSY pulse sequence. For example, in various embodiments one can select the Man4 H2 signal at ca. 4.25 ppm and determine whether this leads to transfer of polarization to an H3 peak at ca. 3.90 ppm (mono-antennary) or ca. 4.10 ppm (bi-antennary).

1D $^1$H selective TOCSY pulse sequences may also be used in other contexts to more clearly assign specific 1D $^1$H peaks. For example, the H1 signal of a galactose residue in a lactosamine extension resonates at ca. 4.57 ppm in our experiments. When selected using a 1D $^1$H selective TOCSY pulse sequence, TOCSY correlations can be used to identify $^1$H-$^1$H scalar correlations within the galactose residue. These $^1$H-$^1$H scalar correlations can then be used to confirm the location of the galactose residue to be within a polylactosamine extension. It will be appreciated that these correlations may alternatively be identified in the context of a different NMR experiment, e.g., without limitation a 2D $^1$H-$^1$H TOCSY experiment.

$^1$H-$^1$H scalar correlations may also be used to identify the presence of a sulfated GlcNAc moiety. Indeed, 6-O-sulfation should give rise to a diagnostic $^1$H chemical shift for H6 and other $^1$H signals around the monosaccharide ring system. While these $^1$H signals may be present within a crowded region of the spectrum, a 2D $^1$H-$^1$H TOCSY or 1D $^1$H selective TOCSY experiment can be used to reveal a pattern of $^1$H-$^1$H scalar correlations, which, taken together, are diagnostic for the 6-O-sulfated GlcNAc.

This approach can also be used to identify the presence of a phosphorylated mannose moiety. Indeed, 6-O-phosphorylation should give rise to a diagnostic $^1$H chemical shift for H6 and other $^1$H signals around the monosaccharide ring system. While these $^1$H signals may be present within a crowded region of the spectrum, the position of the phosphomannose H6 signal can be determined using a $^1$H-$^{31}$P scalar correlation experiment. The remainder of the phosphomannose spin system can then be resolved from the rest of the overlapped portion of the spectrum using a $^{31}$P-$^1$H HSQC-TOCSY pulse sequence which selects magnetization from $^{31}$P-$^1$H and then transfers it to other protons around the phosphomannose ring via a TOCSY sequence. Alternatively, a simple 2D $^1$H-$^1$H TOCSY or selective 1D $^1$H TOCSY experiment can be used to reveal a pattern of $^1$H-$^1$H scalar correlations, which, taken together, are diagnostic for the 6-O-phosphorylated mannose.

It is to be understood that the improvements in resolution that can be obtained using $^1$H-$^1$H scalar correlations will generally apply to any 1D $^1$H signal where the detected proton possesses a sufficiently strong $^1$H-$^1$H scalar coupling with a neighboring proton. Preferably the two coupled protons have different chemical shifts. It is also to be understood that 1D $^1$H, 1D $^1$H selective TOCSY and 2D $^1$H-$^1$H TOCSY spectra can be used separately or in conjunction according to the methods described herein.

$^1$H-$^{13}$C Scalar Correlations

In another aspect, structural characteristics of N-glycans can be identified using $^1$H-$^{13}$C scalar correlations (e.g., without limitation, in a 2D $^1$H-$^{13}$C HSQC spectrum). According to this aspect $^1$H-$^{13}$C scalar correlations are detected for the sample of interest and at least one correlation is identified which is known to be associated with a particular structural characteristic. $^1$H-$^{13}$C scalar correlations (e.g., in a 2D $^1$H-$^{13}$C HSQC spectrum) generally provide even more spectral resolution than $^1$H-$^1$H scalar correlations (e.g., in a 2D $^1$H-$^1$H TOCSY spectrum) since different correlations are now also separated in the $^{13}$C dimension. In the Examples we describe 2D $^1$H-$^{13}$C HSQC spectra that were acquired on a 600 MHz Bruker Avance spectrometer with 5 mm cryoprobe at 27° C. using a sensitivity-enhanced gradient HSQC pulse sequence. A total of 16 points were averaged for each of 1024×256 hyper complex points. The recycle delay was 1.1 s. However, it will be appreciated that the 2D $^1$H-$^{13}$C HSQC spectrum may be obtained using any known pulse sequence and any suitable set of experimental conditions. In a 2D $^1$H-$^{13}$C HSQC experiment, a 'magnetization-transfer delay' present within the pulse sequence enables magnetization to be transferred using the scalar coupling between $^1$H and $^{13}$C that are closely linked by chemical bonds. However, the sensitivity of the HSQC measurement is lower than 1D $^1$H and 2D $^1$H-$^1$H TOCSY experiments due to the low natural abundance of $^{13}$C (about 1%). As a result the data acquisition times for a 2D $^1$H-$^{13}$C HSQC experiment will generally be longer than for a 2D $^1$H-$^1$H TOCSY which will in turn be longer than for a 1D $^1$H experiment. It will be appreciated that shorter data acquisition times may be used in the event the sample includes isotopically enriched N-glycans (i.e., $^{13}$C enriched N-glycans).

As described previously it is to be understood that any NMR experiment may be used to identify $^1$H-$^{13}$C scalar correlations. Thus, without limitation, instead of a 2D $^1$H-$^{13}$C HSQC experiment one could use 2D selective TOCSY HSQC, HMQC, TOCSY HMQC, accordion-HSQC, accordion-HMQC experiments, etc.

For example, in various embodiments it may be advantageous to perform a 2D selective TOCSY $^1$H-$^{13}$C HSQC experiment to resolve individual sugar spin systems when a spectrum is particularly crowded. In one embodiment this experiment may be used to determine acetylation positions of sialic acids, e.g., by comparing $^1$H and $^{13}$C chemical shifts for H7, H8 and/or H9 with those of free sialic acid. Indeed, any of the 3 hydroxyl groups in the C7-C9 side-chain (i.e., CH(OH)—CH(OH)—CH$_2$OH) may be acetylated. If acetylation has occurred, this will result in a significant downfield chemical shift of the CH proton at the acetylation position. The TOCSY experiment will reveal any such significant changes in the chemical shift of these protons, and will therefore reveal which, if any, of these positions are acetylated.

Figure 10:
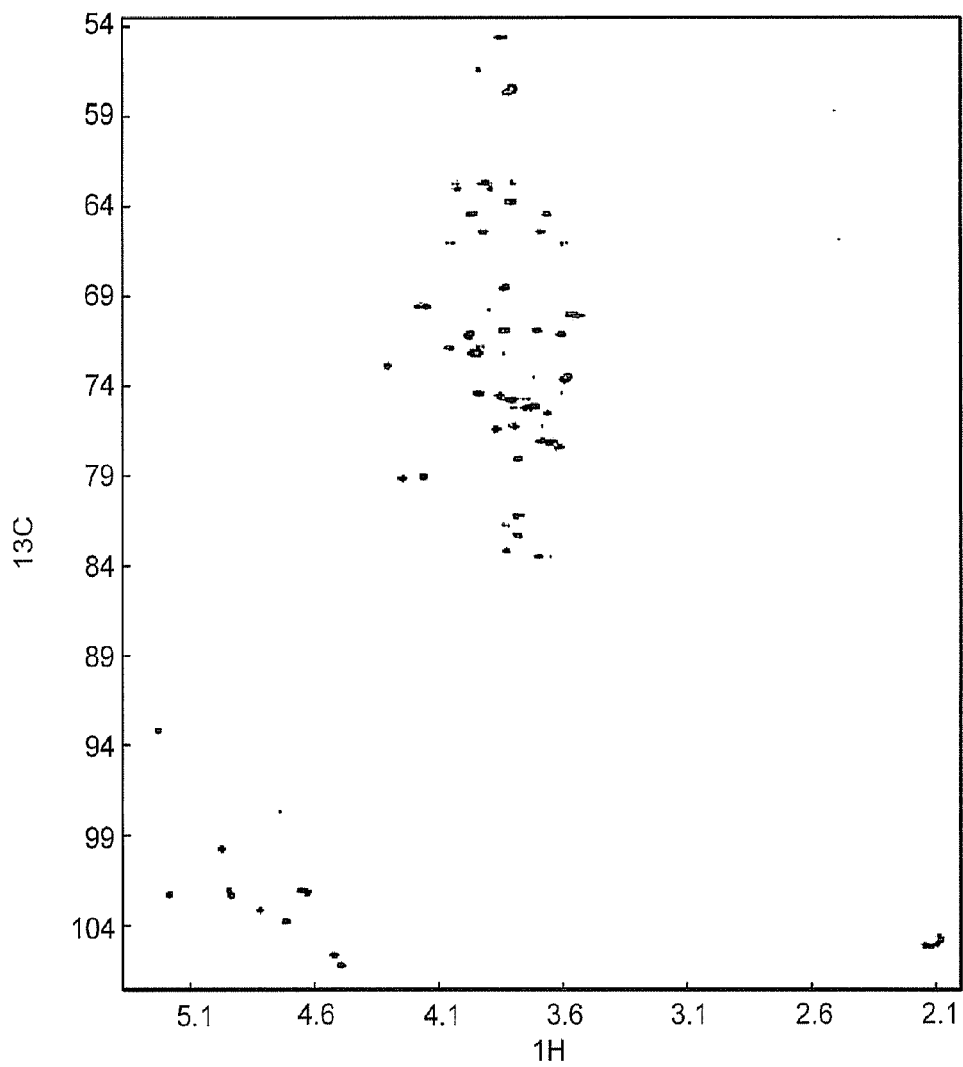
FIG. 10 shows the 2D $^1H$-$^{13}C$ HSQC spectrum of A1F. The spectrum was acquired on a 600 MHz Bruker Avance spectrometer with 5 mm cryoprobe at 27° C. using a sensitivity-enhanced gradient HSQC pulse sequence. A total of 16 points were averaged for each of 1024×256 hyper complex points. The recycle delay was 1.1 s.

For illustrative purposes, the 2D $^1$H-$^{13}$C HSQC spectrum of a model N-glycan (A1F) is shown in FIG. 10. 2D $^1$H-$^{13}$C HSQC spectra may be used quantitatively. A correction factor may be required if the $^1$H-$^{13}$C scalar couplings vary significantly between residues. However, signals from groups which have similar scalar couplings can be directly compared without correction.

Figure 11:
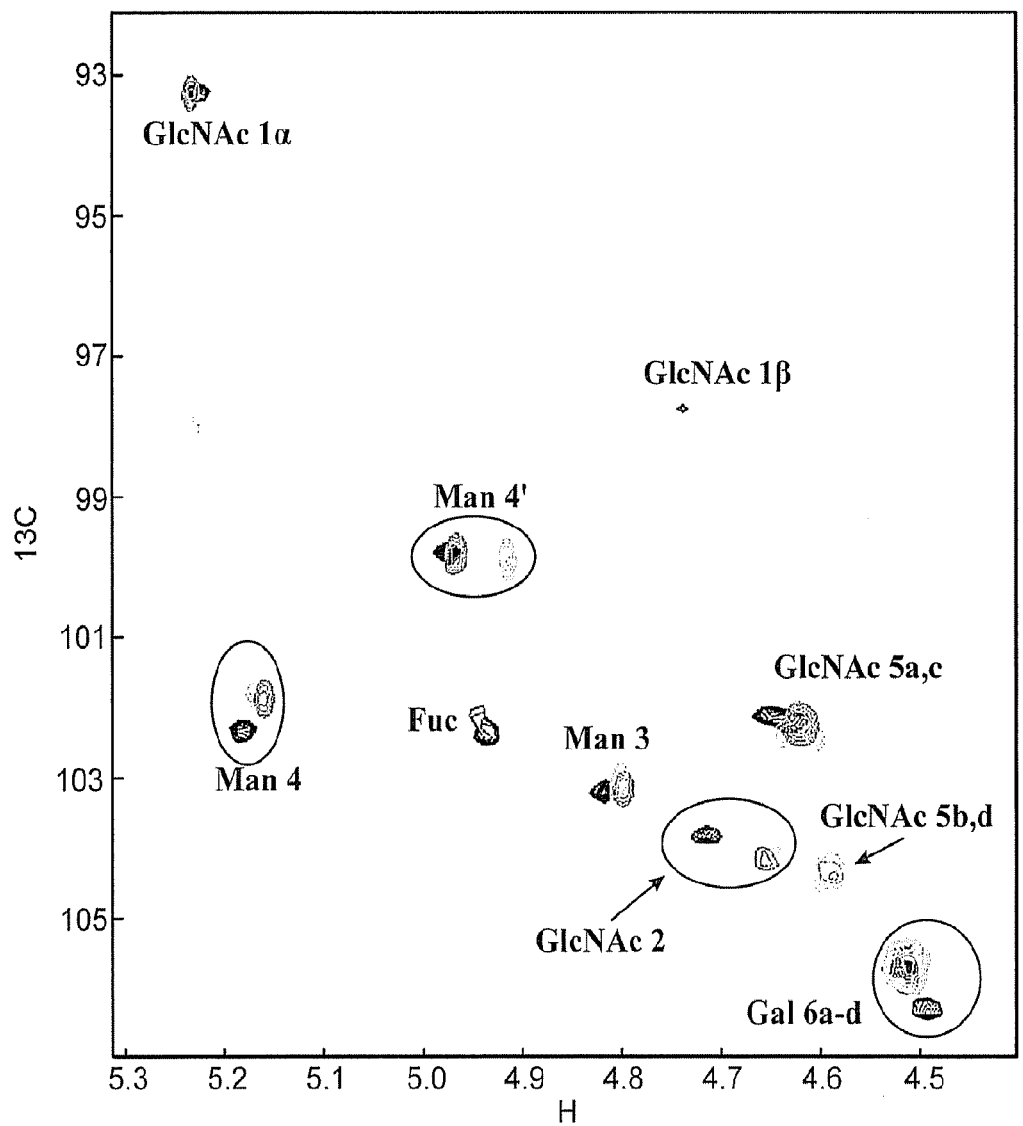
FIG. 11 shows the overlaid 2D $^1H$-$^{13}C$ HSQC spectra of the anomeric regions of A1F (black), NA3 (red), and NA4 (green).
Figure 12:
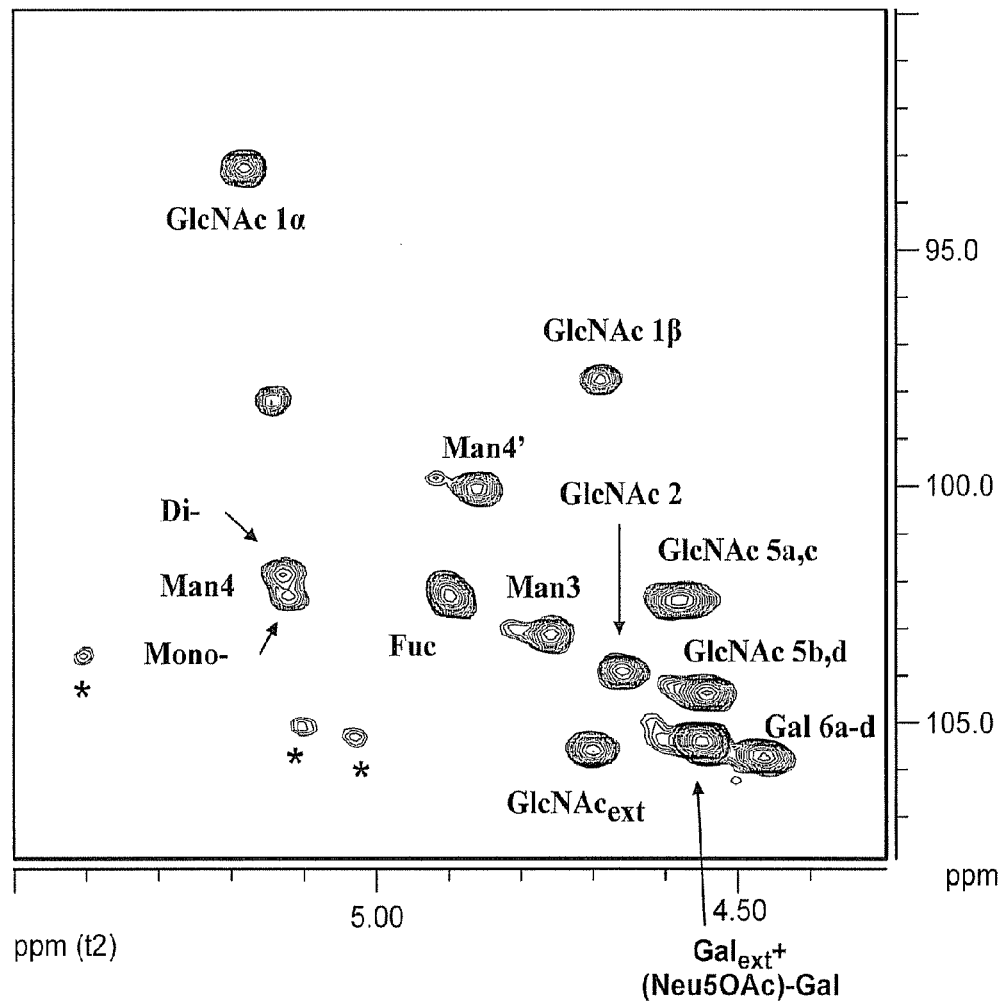
FIG. 12 shows the 2D $^1H$-$^{13}C$ HSQC spectrum of an N-glycan pool, recorded at 27° C., in $D_2O$, with a 600 MHz Bruker Avance spectrometer with 5 mm cryoprobe. The numbering scheme used to identify the residues is indicated in FIG. 1. $GlcNAc_{ext}$ stands for N-acetylglucosamine in lactosamine extension; $Gal_{ext}$ indicates galactose in lactosamine extension. An asterisk (*) indicates signals assigned to oligomannose structures.
Figure 14:
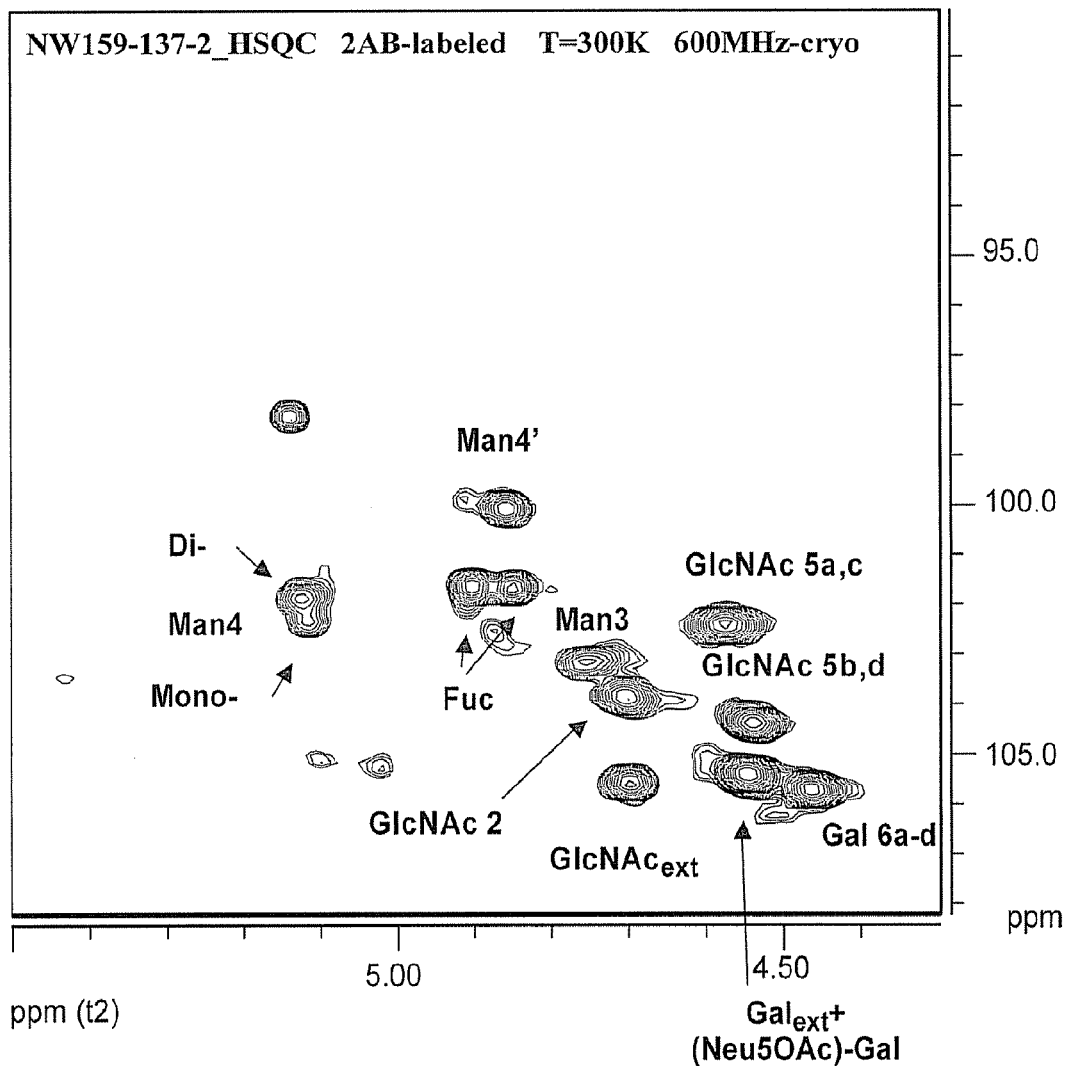
FIG. 14 shows the 2D $^1H$-$^{13}C$ HSQC spectrum of a 2AB-labeled N-glycan pool, recorded at 27° C., in $D_2O$, with a 600 MHz Bruker Avance spectrometer equipped with 5 mm cryoprobe. The numbering scheme used to identify the residues is indicated in FIG. 1. $GlcNAc_{ext}$ stands for N-acetylglucosamine in lactosamine extension; $Gal_{ext}$ indicates galactose in lactosamine extension.

In certain embodiments, the cross-peaks in a 2D $^1$H-$^{13}$C HSQC spectrum may be used to determine the monosaccharide composition of a glycan mixture. In particular, as shown in FIGS. 11, 12 and 14, the anomeric signals for each residue type produce $^1$H-$^{13}$C cross-peaks that are even more resolved than in the 1D $^1$H spectrum. The anomeric signals of Man4 and Man4' (with cross-peaks at $^1$H/$^{13}$C of ca. 5.15 ppm/ca. 102 ppm and ca. 4.95 ppm/ca. 100 ppm, respectively, e.g., see FIG. 11) can be quantified in this manner. The anomeric signals of GlcNAc and Gal may also be used to determine the monosaccharide composition of a glycan mixture (e.g., see cross-peaks at $^1$H/$^{13}$C of ca. 4.50-4.75 ppm/ca. 104-106 ppm in FIG. 11). It will be appreciated that when cross-peaks from GlcNAc and Gal partially overlap, analytical methods (e.g., peak fitting algorithms) may be used in order to extract quantitative information. Similar analytical tools may be used in order to compensate for partial signal attenuation caused by presaturation of the neighboring water signal. Sialic acid lacks an anomeric proton, but can be quantified by the axial and equatorial H3 signals in the upfield region of the spectrum (with cross-peaks at $^1$H/$^{13}$C of ca. 1.7 ppm/ca. 39 ppm and ca. 2.6 ppm/ca. 39 ppm, respectively, data not shown).

Branching at the Man4 and 4' positions is also readily determined by the anomeric chemical shifts of $^1$H-$^{13}$C scalar correlations. For example, as shown by the overlay of 2D $^1$H-$^{13}$C HSQC spectra from various model compounds in FIG. 11 and the spectrum of an N-glycan pool in FIG. 12, the anomeric signal positions of the branching mannose residues are diagnostic of the number of branches at each position. The equivalent analysis by simple 1D $^1$H analysis is difficult as the Man4 $^1$H signal shift between the mono- and di-substituted species is negligible, and the Man4' $^1$H signal suffers from partial overlap with that of fucose. Nonetheless, as discussed above, characteristic $^1$H-$^1$H scalar correlations that are associated with branching at the Man4 position may still be identified within a 1D spectrum by using a selective pulse sequence, e.g., a 1D $^1$H selective TOCSY sequence.

Figure 16:
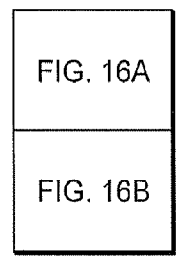
FIG. 16 is a table showing the chemical shifts for various peaks in the spectra of FIGS. 12 and 14.

As shown in FIGS. 11 and 12 and summarized in FIG. 16, the anomeric chemical shifts of $^1$H-$^{13}$C scalar correlations can be used to detect the presence (or the relative ratio based on relative signal integrals) of the following mannose residues and branching patterns in unlabeled N-glycans:

Man4 mono-antennary: $\delta_H$ ca. 5.10-5.15 ppm; $\delta_c$ ca. 102.2-102.6 ppm Man4 bi-antennary: $\delta_H$ ca. 5.10-5.15 ppm; $\delta_c$ ca. 101.7-102.1 ppm Man4' mono-antennary: $\delta_H$ ca. 4.90-4.95 ppm; $\delta_c$ ca. 98.8-99.8 ppm Man4' bi-antennary: $\delta_H$ ca. 4.83-4.88 ppm; $\delta_c$ ca. 99.5-100.5 ppm As shown in FIGS. 11 and 12 and summarized in FIG. 16, the anomeric chemical shifts of $^1$H-$^{13}$C scalar correlations can be also be used to detect the presence (or the relative ratio based on relative signals) of the following core residues in unlabeled N-glycans:

GlcNAc1α: $\delta_H$ ca. 5.15-5.20 ppm; $\delta_c$ ca. 93-94 ppm
GlcNAc1β: $\delta_H$ ca. 4.65-4.70 ppm; $\delta_c$ ca. 97-98 ppm
GlcNac2: $\delta_H$ ca. 4.63-4.68 ppm; $\delta_c$ ca. 103.5-104.5 ppm
Man3: $\delta_H$ ca. 4.72-4.77 ppm; $\delta_c$ ca. 102.7-103.7 ppm The anomeric chemical shifts of $^1$H-$^{13}$C scalar correlations can be also be used to detect and/or quantify GlcNacs in β(1-2) linkages to mannose, GlcNacs in β(1-4) or β(1-6) linkages to mannose and GlcNacs in lactosamine-extensions:

β(1-2) linkages: $\delta_H$ ca. 4.55-4.60 ppm; $\delta_C$ ca. 102-103 ppm
β(1-4) or β(1-6) linkages: $\delta_H$ ca. 4.52-4.58 ppm; $\delta_C$ ca. 104-105 ppm
lactosamine-extensions: $\delta_H$ ca. 4.67-4.72 ppm; $\delta_C$ ca. 105-106 ppm The distinction between these different GlcNAc residues can be seen in FIG. 12 by comparing the chemical shifts of GlcNAc5a,c (i.e., β(1-2) linkages to mannose), GlcNAc5b,d (i.e., β(1-4) linkages to mannose) and GlcNac$_{ext}$.

The anomeric chemical shifts of $^1$H-$^{13}$C scalar correlations can be also be used to detect and/or quantify unsubstituted galactose residues (i.e., no sialic acid), galactose residues with an α(2-3) sialic acid attached, galactose residues with an α(2-6) sialic acid attached, and galactose residues in lactosamine-extensions:

unsubstituted (no sialic acid): $\delta_H$ ca. 4.43-4.48 ppm; $\delta_C$ ca. 105-106 ppm
α(2-3) sialic acid attached: $\delta_H$ ca. 4.52-4.57 ppm; $\delta_C$ ca. 105-106 ppm
α(2-6) sialic acid attached: $\delta_H$ ca. 4.41-4.47 ppm; $\delta_C$ ca. 106-107 ppm
lactosamine-extensions: $\delta_H$ ca. 4.52-4.57 ppm; $\delta_C$ ca. 105-106 ppm Peaks for unsubstituted galactose, galactose in a galactosamine extension or galactose with α(2-3) sialic attached (Neu5OAc) are shown in FIG. 12 (the latter pair overlap). A peak for galactose with α(2-6) sialic attached was observed in a 2D $^1$H-$^{13}$C HSQC spectrum of the model glycan A1F-2AB (data not shown).

The anomeric chemical shifts of $^1$H-$^{13}$C scalar correlations can be also be used to detect and/or quantify oligomannose structures (e.g., in high mannose glycans). Thus, as shown in FIG. 12, in various embodiments, oligomannose structures are associated with one or more $^1$H-$^{13}$C scalar correlations in the following ranges:

$\delta_H$ ca. 5.35-5.45 ppm; $\delta_C$ ca. 103-104 ppm
$\delta_H$ ca. 5.05-5.15 ppm; $\delta_C$ ca. 104.5-105.5 ppm
$\delta_H$ ca. 4.95-5.05 ppm; $\delta_C$ ca. 105-106 ppm In one embodiment, more than one $^1$H-$^{13}$C scalar correlations, e.g., 2 or 3 correlations are observed across these ranges. In one embodiment, 1 or 2 correlations are observed in the following range:

$\delta_H$ ca. 4.90-5.20 ppm; $\delta_C$ ca. 104-106 ppm

The anomeric chemical shifts of $^1$H-$^{13}$C scalar correlations can be also be used to detect and/or quantify fucose residues. For example, as shown in FIG. 12, in various embodiments, core fucose residues in unlabeled N-glycans exhibit a correlation in the following anomeric region:

$\delta_H$ ca. 4.85-4.95 ppm; $\delta_C$ ca. 101-103 ppm

Methyl chemical shifts of $^1$H-$^{13}$C scalar correlations can be also be used to detect and/or quantify fucose residues and in particular to distinguish core and antennary fucose residues. For example, in various embodiments, core and antennary fucose residues in unlabeled N-glycans exhibit a correlation in the following range (data not shown):

core fucose: $\delta_H$ ca. 1.17-1.19 ppm; $\delta_C$ ca. 17.7-18.7 ppm
antennary fucose: $\delta_H$ ca. 1.21-1.24 ppm; $\delta_C$ ca. 17-19 ppm In general it is to be understood that the improvement in resolution that can be obtained via $^1$H-$^{13}$C scalar correlations (e.g., in a 2D $^1$H-$^{13}$C HSQC spectrum) will generally apply to any 1D $^1$H signal where the detected proton possesses a sufficiently large $^1$H-$^{13}$C scalar coupling with a carbon. It is also to be understood that 1D $^1$H chemical shifts, $^1$H-$^1$H scalar correlations and $^1$H-$^{13}$C scalar correlations can be used separately or in conjunction according to the methods described herein.

Analysis of Labeled Glycans

To facilitate the isolation procedure, N-glycan pools are sometimes labeled, e.g., with a fluorophore. FIG. 14 shows the 2D $^1$H-$^{13}$C HSQC spectrum of a 2AB-labeled version of the unlabeled sample that was used in obtaining the spectrum of FIG. 12. The chemical shifts of the $^1$H-$^{13}$C scalar correlations in FIG. 14 are summarized in FIG. 16. As shown in FIG. 16, chemical shifts for certain residues are shifted as a result of the 2AB label, in particular those that are closest to the core (i.e., closest to the point of attachment of the 2AB label). It will be appreciated that these shifted ranges should be used instead of those presented above when analyzing N-glycan mixtures from a 2AB-labeled sample. It will also be appreciated that yet other labels may lead to different chemical shift ranges for each residue type and that these are readily identifiable based on the teachings herein. The present disclosure encompasses methods of analyzing these alternatively labeled N-glycans by NMR.

Figure 13:
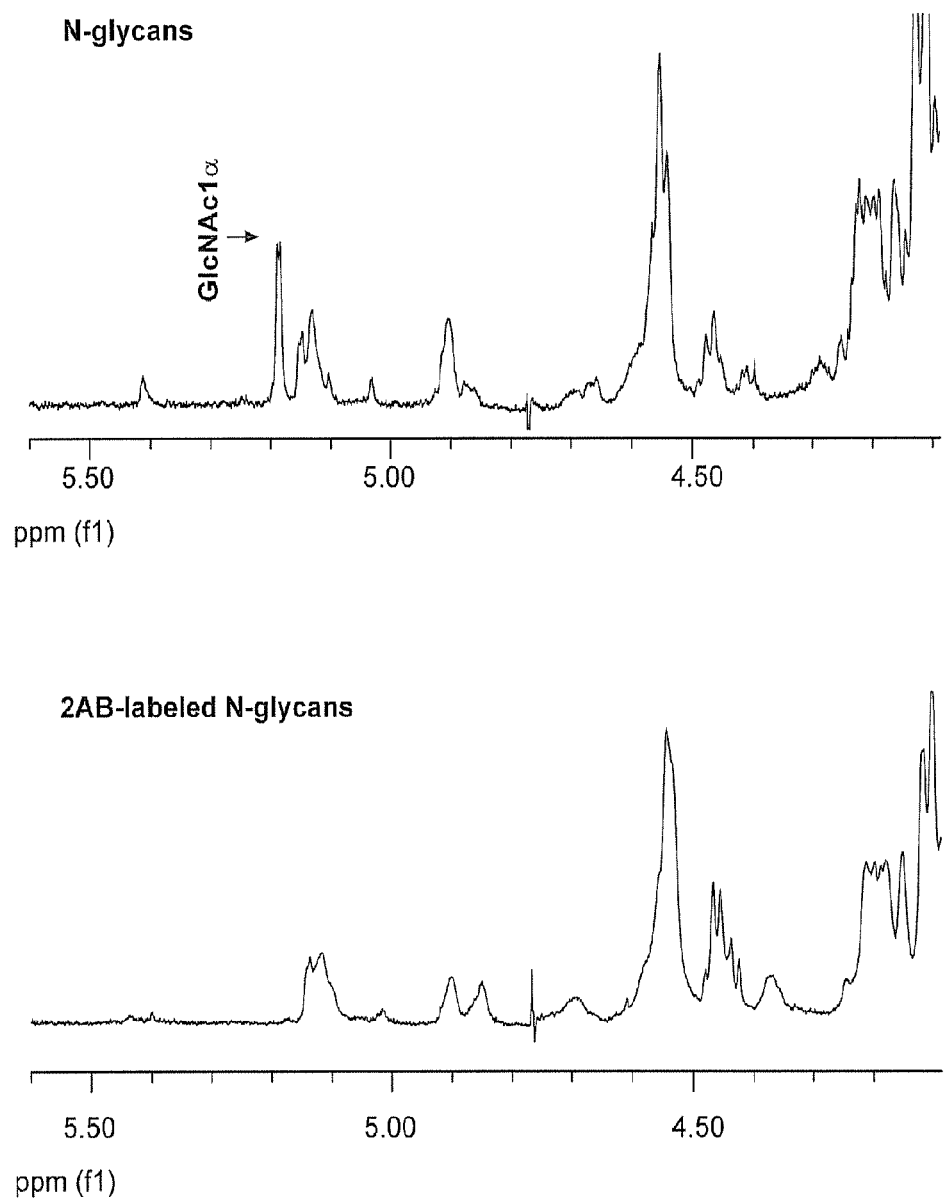
FIG. 13 shows the anomeric region of the 1D $^1H$ spectra of unlabeled and 2-AB labeled N-glycan pools. Spectra were recorded at 600 MHz, 25° C., in $D_2O$.

Typically the labeling reaction will cause the N-glycan NMR spectrum to lose a characteristic signal that can be used as a proxy for measuring the quality and extent of the labeling reaction. For example, FIG. 13 shows that 1D $^1$H-NMR spectra of N-glycans labeled with 2AB lack signals due to GlcNAc1α H1. The level of residual signals due to GlcNAc1α H1 can be used to demonstrate the effectiveness of the 2AB-labeling procedure.

FIG. 14 shows that the same labeling reaction causes the signals due to GlcNAc1α/β in the 2D $^1$H-$^{13}$C HSQC spectrum to disappear. In addition, after 2AB-labeling, Man3 and GlcNAc2 are slightly shifted from their original position (compare FIG. 12 with FIG. 14). Interestingly, the anomeric fucose signal splits into two partially resolved signals (compare FIG. 12 with FIG. 14). A split is also observed in the 2D $^1$H-$^{13}$C HSQC spectrum for the methyl fucose signal (data not shown). Thus, in one embodiment, chemical shifts of $^1$H-$^{13}$C scalar correlations can be also be used to detect and/or quantify 2AB-labeled fucose residues using correlations in the following ranges:

core fucose (anomeric): $\delta_{H'}$ ca. 4.82-4.88 ppm and $\delta_{C'}$ ca. 101-102 ppm $\delta_{H''}$ ca. 4.88-4.93 ppm and $\delta_{C''}$ ca. 101-102 ppm core fucose (methyl): $\delta_{H'}$ ca. 1.15-1.20 ppm and $\delta_{C'}$ ca. 17.7-18.7 ppm $\delta_{H''}$ ca. 1.20-1.25 ppm and $\delta_{C''}$ ca. 17.7-18.7 ppm The split fucose signals are also clearly resolved in a 2D $^1$H-$^1$H TOCSY experiment, where two different signals due to fucose H1/H2 (and H1/H3) cross-peaks can be identified (see FIG. 15). Moreover, two separate signals for fucose —CH$_3$/H5 cross-peaks are also clearly visible (see FIG. 15).

Combination with Enzyme Digestion

In one aspect, one or more of the NMR methods described above can be used in combination with enzymatic treatment, e.g., to elucidate the branching position of a complex glycan.

In some embodiments, the combination of NMR with enzymatic treatments of glycans enables the location of specific antennae to be determined on the glycan of interest. For example, if a glycan contains three sialylated antennae and one non-sialylated antenna, enzymatic treatments can be used that will remove the non-sialylated antenna. This will result in a change of the Man4 or Man4' NMR signals from a biantennary to a monoantennary pattern. The position of attachment of the non-sialylated antenna can therefore be determined from the NMR data.

When treating a sample with different enzymes, treatment may be simultaneous or sequential. In one embodiment, NMR data may be obtained on the sample prior to enzymatic treatment and after each phase of treatment (e.g., in a sequential experiment). In one embodiment, NMR data may be obtained continuously during in situ enzymatic treatment. In situ NMR reduces sample loss and also allows the enzymatic reaction to be monitored in real time, thereby confirming optimal conditions and duration for enzymatic treatment.

Applications

It will be appreciated that the techniques described herein can be utilized in any of a variety of applications. In general, these techniques are useful in any application that involves the structural characterization of N-glycans. Techniques of the present disclosure may be particularly useful in characterizing monosaccharide composition, branching, fucosylation, sulfation, phosphorylation, sialylation linkages ($\alpha$2-3 vs. $\alpha$2-6), presence of impurities and/or efficiency of a labeling procedure (e.g., labeling with a fluorophore such as 2-AB).

Methods of the present disclosure can be applied to glycan mixtures obtained from a wide variety of sources including, but not limited to, therapeutic formulations and biological samples. A biological sample may undergo one or more analysis and/or purification steps prior to or after being analyzed according to the present disclosure. To give but a few examples, in some embodiments, a biological sample is treated with one or more proteases and/or glycosidases (e.g., so that glycans are released); in some embodiments, glycans in a biological sample are labeled with one or more detectable markers or other agents that may facilitate analysis by, for example, mass spectrometry or NMR. Any of a variety of separation and/or isolation steps may be applied to a biological sample in accordance with the present disclosure.

Methods of the present disclosure can be utilized to analyze glycans in any of a variety of states including, for instance, free glycans, glycoconjugates (e.g., glycopeptides, glycolipids, proteoglycans, etc.), or cells or cell components, etc. In one embodiment, the methods are used to analyze a glycan preparation. In one embodiment, the methods are used to analyze a glycoprotein preparation.

Methods of the present disclosure may be used in one or more stages of process development for the production of a therapeutic or other commercially relevant glycoprotein of interest. Non-limiting examples of such process development stages that can employ methods of the present disclosure include cell selection, clonal selection, media optimization, culture conditions, process conditions, and/or purification procedure. Those of ordinary skill in the art will be aware of other process development stages.

The methods can also be utilized to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern.

The methods can also be utilized to assess glycosylation characteristics of cells or cell lines that are being considered for production of a particular desired glycoprotein (for example, even before the cells or cell lines have been engineered to produce the glycoprotein, or to produce the glycoprotein at a commercially relevant level).

In some embodiments of the disclosure, a desired glycosylation pattern for a particular target glycoprotein (e.g., a cell surface glycoprotein) is known, and the technology described herein allows monitoring of culture samples to assess progress of the production along a route known to produce the desired glycosylation pattern. For example, where the target glycoprotein is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible, whether or not it is being produced by exactly the same route. As used herein, "close" refers to a glycosylation pattern having at least about a 75%, 80%, 85%, 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

In some embodiments, a desired glycosylation pattern will be more extensive. For example, in some embodiments, a desired glycosylation pattern shows high (e.g., greater than about 60%, 65%, 70%, 75%, 80%, 85%, 90%, 95% or more) occupancy of glycosylation sites; in some embodiments, a desired glycosylation pattern shows, a high degree of branching (e.g., greater than about 60%, 65%, 70%, 75%, 80%, 85%, 90%, 95% or more have tri or tetraantennary structures).

In some embodiments, a desired glycosylation pattern will be less extensive. For example, in some embodiments, a desired glycosylation pattern shows low (e.g., less than about 35%, 30%, 25%, 20%, 15% or less) occupancy of glycosylation sites; and/or a low degree of branching (e.g., less than about 20%, 15%, 10%, 5%, or less have tri or tetraantennary structures).

In some embodiments, a desired glycosylation pattern will be more extensive in some aspects and less extensive than others. For example, it may be desirable to employ a cell line that tends to produce glycoproteins with long, unbranched oligosaccharide chains. Alternatively, it may be desirable to employ a cell line that tends to produce glycoproteins with short, highly branched oligosaccharide chains.

In some embodiments, a desired glycosylation pattern will be enriched for a particular type of glycan structure. For example, in some embodiments, a desired glycosylation pattern will have low levels (e.g., less than about 20%, 15%, 10%, 5%, or less) of high mannose or hybrid structures, high (e.g., more than about 60%, 65%, 70%, 75%, 80%, 85%, 90% or more) levels of high mannose structures, or high (e.g., more than about 60%, 65%, 70%, 75%, 80%, 85%, 90% or more; for example at least one per glycoprotein) or low (e.g., less than about 20%, 15%, 10%, 5%, or less) levels of phosphorylated high mannose.

In some embodiments, a desired glycosylation pattern will include at least about one sialic acid. In some embodiments, a desired glycosylation pattern will include a high (e.g., greater than about 60%, 65%, 70%, 75%, 80%, 85%, 90%, 95% or more) level of termini that are sialylated. In some embodiments, a desired glycosylation pattern that includes sialylation will show at least about 85%, 90%, 95% or more N-acetylneuraminic acid and/or less than about 15%, 10%, 5% or less N-glycolylneuraminic acid.

In some embodiments, a desired glycosylation pattern shows specificity of branch elongation (e.g., greater than about 50%, 55%, 60%, 65%, 70% or more of extension is on α1,6 mannose branches, or greater than about 50%, 55%, 60%, 65%, 70% or more of extension is on α1,3 mannose branches).

In some embodiments, a desired glycosylation pattern will include a low (e.g., less than about 20%, 15%, 10%, 5%, or less) or high (e.g., more than about 60%, 65%, 70%, 75%, 80%, 85%, 90%, 95%, or more) level of core fucosylation.

Whether or not monitoring production of a particular target protein for quality control purposes, the methods may be utilized, for example, to monitor glycosylation at particular stages of development, or under particular growth conditions.

In some particular embodiments, methods described herein can be used to characterize and/or control or compare the quality of therapeutic products. To give but one example, the present methodologies can be used to assess glycosylation in cells producing a therapeutic protein product. Particularly given that glycosylation can often affect the activity, bioavailability, or other characteristics of a therapeutic protein product, methods for assessing cellular glycosylation during production of such a therapeutic protein product are particularly desirable. Among other things, the methods can facilitate real time analysis of glycosylation in production systems for therapeutic proteins.

Representative therapeutic glycoprotein products whose production and/or quality can be monitored in accordance with the present disclosure include, for example, any of a variety of hematologic agents (including, for instance, erythropoietins, blood-clotting factors, etc.), interferons, colony stimulating factors, antibodies, enzymes, and hormones.

Representative commercially available glycoprotein products include, for example:

| Protein Product | Reference Drug |
|---|---|
| interferon gamma-1b | Actimmune ® |
| alteplase; tissue plasminogen activator | Activase ®/Cathflo ® |
| Recombinant antihemophilic factor | Advate |
| human albumin | Albutein ® |
| laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| bivalirudin | Angiomax ® |
| darbepoetin alfa | Aranesp ™ |
| bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| rasburicase | Elitek ® |
| etanercept | Enbrel ® |
| epoietin alfa | Epogen ® |
| cetuximab | Erbitux ™ |
| algasidase beta | Fabrazyme ® |
| urofollitropin | Fertinex ™ |
| follitropin beta | Follistim ™ |
| teriparatide | Forteo ® |
| human somatropin | GenoTropin ® |
| glucagon | GlucaGen ® |
| follitropin alfa | Gonal-F ® |
| antihemophilic factor | Helixate ® |
| Antihemophilic Factor; Factor XIII | Hemofil ® |
| insulin | Humalog ® |
| antihemophilic factor/von Willebrand factor complex-human | Humate-P ® |
| somatotropin | Humatrope ® |
| adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| palifermin | Kepivance |
| anakinra | Kineret ™ |
| antihemophilic factor | Kogenate ® FS |
| insulin glargine | Lantus ® |
| granulocyte macrophage colony-stimulating factor | Leukine ®/Leukine ® Liquid |
| lutropin alfa, for injection | Luveris |
| OspA lipoprotein | LYMErix ™ |
| ranibizumab | Lucentis ® |
| gemtuzumab ozogamicin | Mylotarg ™ |
| galsulfase | Naglazyme ™ |
| nesiritide | Natrecor ® |
| pegfilgrastim | Neulasta ™ |
| oprelvekin | Neumega ® |
| filgrastim | Neupogen ® |
| fanolesomab | NeutroSpec ™ (formerly LeuTech ®) |
| somatropin [rDNA] | Norditropin ®/Norditropin Nordiflex ® |
| insulin; zinc suspension; | Novolin L ® |
| insulin; isophane suspension | Novolin N ® |
| insulin, regular; | Novolin R ® |
| insulin | Novolin ® |
| coagulation factor VIIa | NovoSeven ® |
| somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| human chorionic gonadotropin | Ovidrel ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| aldesleukin | Proleukin, IL-2 ® |
| somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| lepirudin | Refludan ® |
| infliximab | Remicade ® |
| abciximab | ReoPro ™ |
| reteplase | Retavase ™ |
| rituximab | Rituxan ™ |
| interferon alfa-2a | Roferon-A ® |
| somatropin | Saizen ® |
| synthetic porcine secretin | SecreFlo ™ |
| basiliximab | Simulect ® |

-continued

| Protein Product | Reference Drug |
|---|---|
| eculizumab | Soliris ® |
| pegvisomant | Somavert ® |
| Palivizumab; recombinantly produced, humanized mAb | Synagis ™ |
| thyrotropin alfa | Thyrogen ® |
| tenecteplase | TNKase ™ |
| natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| daclizumab | Zenapax ® |
| ibritumomab tiuxetan | Zevalin ™ |
| Somatotropin | Zorbtive ™ (Serostim ®) |

In some embodiments, the disclosure provides methods in which glycans from different sources or samples are compared with one another. In certain embodiments, the disclosure provides methods used to monitor the extent and/or type of glycosylation occurring in different cell cultures. In some such examples, multiple samples from the same source are obtained over time, so that changes in glycosylation patterns (and particularly in cell surface glycosylation patterns) are monitored. In some embodiments, one of the samples is a historical sample or a record of a historical sample. In some embodiments, one of the samples is a reference sample. For example, in certain embodiments, methods are provided herein which can be used to monitor the extent and/or type of glycosylation occurring in different cell cultures.

In some embodiments, glycans from different cell culture samples prepared under conditions that differ in one or more selected parameters (e.g., cell type, culture type [e.g., continuous feed vs batch feed, etc.], culture conditions [e.g., type of media, presence or concentration of particular component of particular medium(a), osmolarity, pH, temperature, timing or degree of shift in one or more components such as osmolarity, pH, temperature, etc.], culture time, isolation steps, etc.) but are otherwise identical, are compared, so that effects of the selected parameter(s) on glycosylation patterns are determined. In certain embodiments, glycans from different cell culture samples prepared under conditions that differ in a single selected parameter are compared so that effect of the single selected parameter on glycosylation patterns is determined. Among other applications, therefore, use of techniques as described herein may facilitate determination of the effects of particular parameters on glycosylation patterns in cells.

In some embodiments, glycans from different batches of a glycoprotein of interest (e.g., a therapeutic glycoprotein), whether prepared by the same method or by different methods, and whether prepared simultaneously or separately, are compared. In such embodiments, the methods facilitate quality control of glycoprotein preparation. Alternatively or additionally, some such embodiments facilitate monitoring of progress of a particular culture producing a glycoprotein of interest (e.g., when samples are removed from the culture at different time points and are analyzed and compared to one another). In any of these embodiments, features of the glycan analysis can be recorded, for example in a quality control record. As indicated above, in some embodiments, a comparison is with a historical record of a prior or standard batch and/or with a reference sample of glycoprotein.

In certain embodiments, the methods may be utilized in studies to modify the glycosylation characteristics of a cell, for example to establish a cell line and/or culture conditions with one or more desirable glycosylation characteristics. Such a cell line and/or culture conditions can then be utilized, if desired, for production of a particular target glycoconjugate (e.g., glycoprotein) for which such glycosylation characteristic(s) is/are expected to be beneficial.

In certain embodiments, techniques of the present disclosure are applied to glycans that are present on the surface of cells. In some such embodiments, the analyzed glycans are substantially free of non-cell-surface glycans. In some such embodiments, the analyzed glycans, when present on the cell-surface, are present in the context of one or more cell-surface glycoconjugates (e.g., glycoproteins or glycolipids).

In some particular embodiments, cell-surface glycans are analyzed in order to assess glycosylation of one or more target glycoproteins of interest, particularly where such target glycoproteins are not cell-surface glycoproteins. Such embodiments can allow one to monitor glycosylation of a target glycoprotein without isolating the glycoprotein itself. In certain embodiments, the present disclosure provides methods of using cell-surface glycans as a readout of or proxy for glycan structures on an expressed glycoprotein of interest. In certain embodiments, such methods include, but are not limited to, post process, batch, screening or "in line" measurements of product quality. Such methods can provide for an independent measure of the glycosylation pattern of a produced glycoprotein of interest using a byproduct of the production reaction (e.g., the cells) without requiring the use of destruction of any produced glycoprotein. Furthermore, methods of the present disclosure can avoid the effort required for isolation of product and the potential selection of product glycoforms that may occur during isolation.

In certain embodiments, techniques of the present disclosure are applied to glycans that are secreted from cells. In some such embodiments, the analyzed glycans are produced by cells in the context of a glycoconjugate (e.g., a glycoprotein or glycolipid).

According to the present disclosure, techniques described herein can be used to detect desirable or undesirable glycans, for example to detect or quantify the presence of one or more contaminants in a product, or to detect or quantify the presence of one or more active or desired species.

In various embodiments the methods can be used to detect biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time.

In certain embodiments, methods described herein facilitate detection of glycans that are present at very low levels in a source (e.g., a biological sample), e.g., at levels no more than 10%, 8%, 6%, 4%, 2% or 1% of the sample composition). In such embodiments, it is possible to detect and/or optionally quantify the levels of glycans comprising between 0.1% and 5%, e.g., between 0.1% and 2%, e.g., between 0.1% and 1% of a glycan preparation. In certain embodiments, it is possible to detect and/or optionally quantify the levels of glycans at between about 0.1 fmol to about 1 mmol.

In some embodiments, techniques described herein may be combined with one or more other technologies for the detection, analysis, and or isolation of glycans or glycoconjugates. For example, without limitation, the glycans may be separated by any chromatographic technique prior to analysis. The glycans may be further analyzed by a different technique, e.g., mass spectrometry.

In some embodiments, the glycans can be analyzed by chromatographic methods, including but not limited to, liquid chromatography (LC), high performance liquid chromatography (HPLC), ultra performance liquid chromatography (UPLC), thin layer chromatography (TLC), amide column chromatography, and combinations thereof.

In some embodiments, the glycans can be analyzed by mass spectrometry (MS) and related methods, including but not limited to, tandem MS, LC-MS, LC-MS/MS, matrix assisted laser desorption ionisation mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, the glycans can be analyzed by electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

The methods will be more specifically illustrated with reference to the following examples. However, it should be understood that the methods are not limited by these examples in any manner.

EXAMPLES

Example 1

1D $^1$H spectra of (a) A1F, (b) NA3, (c) NA4 and (d) a mixture of N-glycans were acquired on a 600 MHz Bruker Avance spectrometer with 5 mm cryoprobe at 27° C. with presaturation of the water resonance. The structures of A1F, NA3 and NA4 are shown in FIG. 2. Each spectrum was obtained by signal averaging 16 to 256 scans. The recycle delay was 14 s. The resulting 1D $^1$H spectra are shown in FIG. 5.

Example 2

Figure 6:
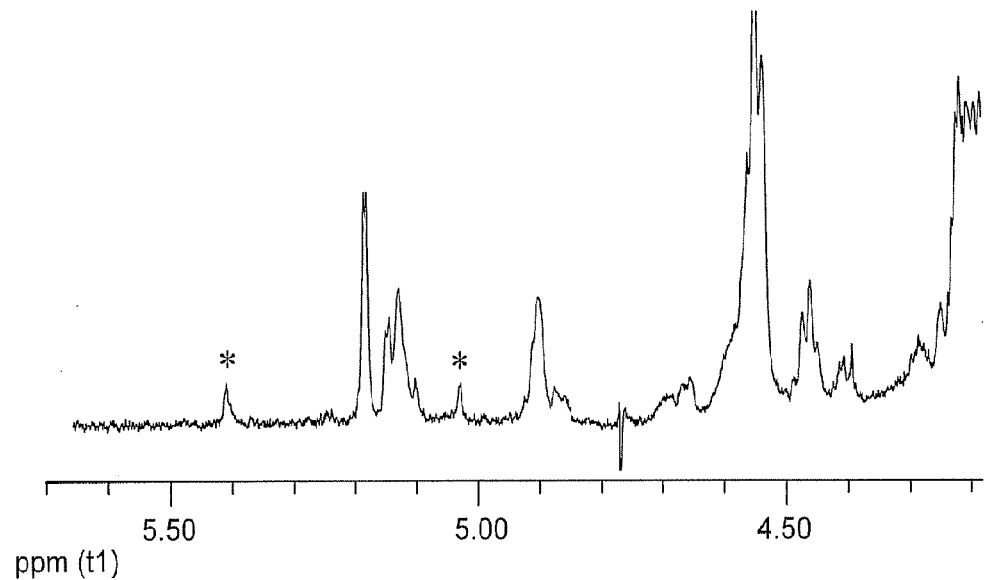
FIG. 6 shows the anomeric region of the 1D $^1H$ spectrum of a mixture of N-glycans. Potential oligomannose structures are indicated with an asterisk (*).

The 1D $^1$H spectra of mixtures of N-glycans were acquired on a 600 MHz Bruker Avance spectrometer with 5 mm cryoprobe, at 25° C., with presaturation of the water resonance. FIG. 6 shows the anomeric region of one such spectrum. Potential oligomannose structures are indicated with an asterisk (*). FIG. 7 shows the methyl region of another such spectrum. Specific assignments are indicated.

Example 3

The 2D $^1$H-$^1$H TOCSY spectrum of the model N-glycans A1F, NA3 and NA4 (see FIG. 3) were acquired on a 600 MHz Bruker Avance spectrometer with 5 mm cryoprobe at 27° C. using 120 ms MLEV-17 mixing. A total of 4 points were averaged for each of 4096×256 hypercomplex points. The recycle delay was 1.4 s. The resulting spectrum for A1F is shown in FIG. 8. FIG. 9 shows the overlaid 2D $^1$H-$^1$H TOCSY spectra of the anomeric regions of A1F (black), NA3 (red), and NA4 (green). The H2/H3 cross-peak position of Man4 is diagnostic of branching, with the only monosubstituted species, A1F, showing a distinct shift from the others.

Example 5

The 2D $^1$H-$^{13}$C HSQC spectrum of the model N-glycan A1F, NA3 and NA4 (see FIG. 3) were acquired on a 600 MHz Bruker Avance spectrometer with 5 mm cryoprobe at 27° C. using a sensitivity-enhanced gradient HSQC pulse sequence. A total of 16 points were averaged for each of 1024×256 hyper complex points. The recycle delay was 1.1 s. The resulting spectrum for A1F is shown in FIG. 10. FIG. 11 shows the overlaid 2D $^1$H-$^{13}$C HSQC spectra of the anomeric regions of A1F (black), NA3 (red), and NA4 (green).

Example 6

The 2D $^1$H-$^{13}$C HSQC spectrum of an N-glycan pool was recorded at 27° C., in $D_2O$, with a 600 MHz Bruker Avance spectrometer with 5 mm cryoprobe. The resulting spectrum is shown in FIG. 12. The numbering scheme used to identify the residues is indicated in FIG. 2. $GlcNAc_{ext}$ stands for N-acetylglucosamine in lactosamine extension; $Gal_{ext}$ indicates galactose in lactosamine extension. An asterisk (*) indicates signals assigned to oligomannose structures. FIG. 16 provides the chemical shifts for various peaks in the spectrum of FIG. 12.

Example 7

The 1D $^1$H spectra of unlabeled and 2-AB labeled N-glycan pools were recorded at 600 MHz, 25° C., in $D_2O$. FIG. 13 compares the anomeric region of these spectra. The spectrum of N-glycans labeled with 2-AB lack signals due to GlcNAc1α H1.

Example 8

The 2D $^1$H-$^{13}$C HSQC spectrum of a 2AB-labeled N-glycan pool was recorded at 27° C., in $D_2O$, with a 600 MHz Bruker Avance spectrometer equipped with 5 mm cryoprobe. The resulting spectrum is shown in FIG. 14. The numbering scheme used to identify the residues is indicated in FIG. 2. $GlcNAc_{ext}$ stands for N-acetylglucosamine in lactosamine extension; $Gal_{ext}$ indicates galactose in lactosamine extension. FIG. 16 provides the chemical shifts for various peaks in the spectrum of FIG. 14.

Example 9

The 2D $^1$H-$^1$H TOCSY spectrum of a 2AB-labeled N-glycan pool was acquired on a 600 MHz Bruker Avance spectrometer equipped with 5 mm cryoprobe at 25° C. in $D_2O$. The resulting spectrum is shown in FIG. 15. Fucose cross-peaks are indicated.

EQUIVALENTS

All literature and similar material cited in this application, including, but not limited to, patents, patent applications, articles, books, treatises, and web pages, regardless of the format of such literature and similar materials, are expressly incorporated by reference in their entirety. In the event that one or more of the incorporated literature and similar materials differs from or contradicts this application, including but not limited to defined terms, term usage, described techniques, or the like, this application controls.

The section headings used herein are for organizational purposes only and are not to be construed as limiting the subject matter described in any way.

While the methods have been described in conjunction with various embodiments and examples, it is not intended that the methods be limited to such embodiments or examples. On the contrary, the present disclosure encompasses various alternatives, modifications, and equivalents, as will be appreciated by those of skill in the art.

While the methods have been particularly shown and described with reference to specific illustrative embodiments, it should be understood that various changes in form and detail may be made without departing from the spirit and scope of the present disclosure. Therefore, all embodiments that come within the scope and spirit of the present disclosure, and equivalents thereto, are intended to be claimed. The claims, descriptions and diagrams of the methods, systems, and assays of the present disclosure should not be read as limited to the described order of elements unless stated to that effect.

What is claimed is:

1. A method for characterizing a mixture of N-glycans by NMR comprising steps of:
   providing a sample that includes a mixture of N-glycans;
   identifying whether the sample produces an NMR signal that is associated with a structural characteristic of an N-glycan, wherein:
   (i) the structural characteristic is an oligomannose structure and the step of identifying comprises determining whether the sample produces a $^1$H signal with a chemical shift in the range of ca. 4.5 ppm to ca. 5.5 ppm;
   (ii) the structural characteristic is a GlcNAc or sialic acid residue and the step of identifying comprises determining whether the sample produces a $^1$H signal corresponding to an acetyl methyl nucleus of a GlcNAc or sialic acid residue;
   (iii) the structural characteristic is a sialic acid residue and the step of identifying comprises determining whether the sample produces a $^1$H signal corresponding to an axial or equatorial H3 nucleus of a sialic acid residue;
   (iv) the structural characteristic is a sialic acid residue with an α2-3 linkage and the step of identifying comprises determining whether the sample produces a $^1$H signal corresponding to an axial H3 nucleus of a sialic acid residue;
   (v) the structural characteristic is a sialic acid residue with an α2-6 linkage and the step of identifying comprises determining whether the sample produces a $^1$H signal corresponding to an axial H3 nucleus of a sialic acid residue;
   (vi) the structural characteristic is di- or tri-acetylated NeuAc and the step of identifying comprises determining whether the sample produces a $^1$H signal with a chemical shift at ca. 2.15 ppm;
   (vii) the structural characteristic is a fucose residue and the step of identifying comprises determining whether the sample produces a $^1$H signal corresponding to a methyl nucleus of a fucose residue;
   (viii) the structural characteristic is a sialic acid and the step of identifying comprises determining whether the sample produces a $^1$H-$^1$H scalar correlation between the H3 axial and H3 equatorial nuclei of a sialic acid;
   (ix) wherein the structural characteristic is a mono-antennary Man4 residue and the step of identifying comprises determining whether the sample produces a $^1$H-$^1$H scalar correlation between the H2 and H3 nuclei of a Man4 residue;
   (x) the structural characteristic is a bi-antennary Man4 residue and the step of identifying comprises determining whether the sample produces a $^1$H-$^1$H scalar correlation between the H2 and H3 nuclei of a Man4 residue;
   (xi) the structural characteristic is a galactose residue in a lactosamine extension and the step of identifying comprises determining the chemical shifts of a $^1$H-$^1$H scalar correlation between the H1 nucleus and another nucleus of a galactose residue;
   (xii) the structural characteristic is a sulfated GlcNac residue and the step of identifying comprises determining the chemical shifts of a $^1$H-$^1$H scalar correlation between the H6 nucleus and another nucleus of a GlcNac residue;
   (xii) the structural characteristic is a phosphorylated mannose residue and the step of identifying comprises determining the chemical shifts of a $^1$H-$^1$H scalar correlation between the H6 nucleus and another nucleus of a mannose residue;
   (xiv) the structural characteristic is a core fucose residue and the step of identifying comprises determining the chemical shifts of a $^1$H-$^{13}$C scalar correlation for the anomeric nucleus of a GlcNAc2 residue;
   (xv) the structural characteristic is a sialic acid residue and the step of identifying comprises determining whether the sample produces a $^1$H-$^{13}$C scalar correlation with chemical shifts corresponding to an axial H3 nucleus of a sialic acid residue;
   (xvi) the structural characteristic is a sialic acid residue and the step of identifying comprises determining whether the sample produces a $^1$H-$^{13}$C scalar correlation with chemical shifts corresponding to an equatorial H3 nucleus of a sialic acid residue;
   (xvii) the structural characteristic is an acetylated sialic acid residue and the step of identifying comprises determining the $^1$H chemical shift of a $^1$H-$^{13}$C scalar correlation of the H7, H8 and/or H9 nuclei of a sialic acid residue;
   (xviii) the structural characteristic is a Man4 residue and the step of identifying comprises determining the chemical shifts of a $^1$H-$^{13}$C scalar correlation corresponding to an anomeric nucleus of a Man4 residue;
   (xix) the structural characteristic is a mono- or bi-antennary Man4 residue and the step of determining comprises determining whether the Man4 residue is mono-antennary or bi-antennary based on the chemical shifts of the $^1$H-$^{13}$C scalar correlation;
   (xx) the structural characteristic is a Man4' residue and the step of identifying comprises determining whether the sample produces a $^1$H-$^{13}$C scalar correlation with chemical shifts corresponding to an anomeric nucleus of a Man4' residue;
   (xxi) the structural characteristic is a mono- or bi-antennary Man4' residue and the step of determining comprises determining whether the Man4' residue is mono-antennary or bi-antennary based on the chemical shifts of the $^1$H-$^{13}$C scalar correlation;
   (xxii) the structural characteristic is a GlcNAc1 residue and the step of identifying comprises determining whether the sample produces a $^1$H-$^{13}$C scalar correlation with chemical shifts corresponding to an anomeric nucleus of a GlcNAc1 residue;
   (xxiii) the structural characteristic is a GlcNAc2 residue and the step of identifying comprises determining whether the sample produces a $^1$H-$^{13}$C scalar correlation with chemical shifts corresponding to an anomeric nucleus of a GlcNAc2 residue;
   (xxiv) the structural characteristic is a Man3 residue and the step of identifying comprises determining whether the sample produces a $^1$H-$^{13}$C scalar correlation with chemical shifts corresponding to an anomeric nucleus of a Man3 residue;

(xxv) the structural characteristic is a GlcNac residue with a β(1-2) linkage to mannose and the step of identifying comprises determining whether the sample produces a $^1$H-$^{13}$C scalar correlation with chemical shifts corresponding to an anomeric nucleus of a GlcNac residue with a β(1-2) linkage to mannose;

(xxvi) the structural characteristic is a GlcNAc residue with a β(1-4) or β(1-6) linkage to mannose and the step of identifying comprises determining whether the sample produces a $^1$H-$^{13}$C scalar correlation with chemical shifts corresponding to an anomeric nucleus of a GlcNAc residue with a β(1-4) or β(1-6) linkage to mannose;

(xxvii) the structural characteristic is a GlcNAc residue in a lactosamine extension and the step of identifying comprises determining whether the sample produces a $^1$H-$^{13}$C scalar correlation with chemical shifts corresponding to an anomeric nucleus of a GlcNac residue in a lactosamine extension;

(xxviii) the structural characteristic is an unsubstituted galactose residue and the step of identifying comprises determining whether the sample produces a $^1$H-$^{13}$C scalar correlation with chemical shifts corresponding to an anomeric nucleus of an unsubstituted galactose residue;

(xxix) the structural characteristic is a galactose residue with an α(2-3) sialic acid attached and the step of identifying comprises determining whether the sample produces a $^1$H-$^{13}$C scalar correlation with chemical shifts corresponding to an anomeric nucleus of a galactose residue with an α(2-3) sialic acid attached;

(xxx) the structural characteristic is a galactose residue with an α(2-6) sialic acid attached and the step of identifying comprises determining whether the sample produces a $^1$H-$^{13}$C scalar correlation with chemical shifts corresponding to an anomeric nucleus of a galactose residue with an α(2-6) sialic acid attached;

(xxxi) the structural characteristic is a galactose residue in a lactosamine extension and the step of identifying comprises determining whether the sample produces a $^1$H-$^{13}$C scalar correlation with chemical shifts corresponding to an anomeric nucleus of a galactose residue in a lactosamine extension;

(xxxii) the structural characteristic is an oligomannose structure and the step of identifying comprises determining whether the sample produces a $^1$H-$^{13}$C scalar correlation with chemical shifts corresponding to an anomeric nucleus of an oligomannose structure;

(xxxiii) the structural characteristic is a core fucose residue and the step of identifying comprises determining whether the sample produces a $^1$H-$^{13}$C scalar correlation with chemical shifts corresponding to an anomeric nucleus of a core fucose residue;

(xxxiv) the structural characteristic is a core fucose residue and the step of identifying comprises determining whether the sample produces a $^1$H-$^{13}$C scalar correlation with chemical shifts corresponding to a methyl nucleus of a core fucose residue;

(xxxv) the structural characteristic is an antennary fucose residue and the step of identifying comprises determining whether the sample produces a $^1$H-$^{13}$C scalar correlation with chemical shifts corresponding to a methyl nucleus of an antennary fucose residue;

(xxxvi) the structural characteristic is a label attached to GlcNAc1 and the step of identifying comprises determining whether the sample produces a $^1$H signal corresponding to GlcNAc1α H1;

(xxxvii) the structural characteristic is a label attached to GlcNAc1 and the step of identifying comprises determining whether the sample produces a split $^1$H-$^1$H scalar correlation corresponding to fucose H1/H2 H1/H3 or —CH$_3$/H5 nuclei;

(xxxviii) the structural characteristic is a label attached to GlcNAc1 and the step of identifying comprises determining whether the sample produces a $^1$H-$^{13}$C scalar correlation corresponding to an anomeric nucleus of GlcNAc1α or GlcNAc1β;

(xxxix) the structural characteristic is a label attached to GlcNAc1 and the step of identifying comprises determining the chemical shifts of a $^1$H-$^{13}$C scalar correlation corresponding to an anomeric nucleus of a GlcNAc2 or Man3 residue;

(xxxx) the structural characteristic is a label attached to GlcNAc1 and the step of identifying comprises determining whether the sample produces a split $^1$H-$^{13}$C scalar correlation corresponding to an anomeric fucose nucleus; or (xxxxi) the structural characteristic is a label attached to GlcNAc1 and the step of identifying comprises determining whether the sample produces a split $^1$H-$^{13}$C scalar correlation corresponding to a methyl fucose nucleus; and determining whether the sample does or does not include an N-glycan with the structural characteristic in light of the step of identifying.

2. The method of claim 1, wherein the step of identifying comprises
obtaining one or more of a 2D NMR spectrum of the sample;
a 2D $^1$H-$^1$H TOCSY NMR spectrum of the sample;
a 1D selective $^1$H TOCSY NMR spectrum of the sample;
or a 2D $^1$H-$^{13}$C HSQC NMR spectrum of the sample.

3. The method of claim 1, wherein the structural characteristic is a label attached to an N-glycan and the step of identifying comprises determining whether the sample produces a scalar correlation corresponding to said N-glycan.

4. The method of claim 1, further comprising steps of treating the sample with a digestive enzyme to produce a digested sample and repeating the step of identifying with the digested sample.

5. The method of claim 1, further comprising determining the composition and structure of an N-glycan in the sample.

6. The method of claim 5, wherein information from at least one other analytical test on the sample is used to determine the composition and structure of the N-glycan.

7. The method of claim 1, further comprising a step of quantifying the amount of N-glycans in the sample that have the structural characteristic.

8. The method of claim 1, further comprising repeating the method with a second different sample and comparing the results obtained with the different samples.

9. The method of claim 1, wherein the sample was obtained by enzymatic digestion of a glycoprotein preparation.

10. The method of claim 9, wherein the glycoprotein preparation is a pharmaceutical product.

11. The method of claim 10, wherein the step of detecting comprises detecting at least one NMR signal that is associated with a structural characteristic of an N-glycan, as shown, for example, in FIGS. 6-14.

12. The method of claim 11, wherein the step of detecting comprises detecting at least two NMR signals that are associated with structural characteristics of N-glycans.

13. The method of claim 11, wherein the step of detecting comprises detecting at least three NMR signals that are associated with structural characteristics of N-glycans.

14. The method of claim 1, wherein the structural characteristic is an oligomannose structure and the step of identifying comprises determining whether the sample produces a $^1H$ signal with a chemical shift in the range of ca. 4.5 ppm to ca. 5.5 ppm.

15. The method of claim 1, wherein the structural characteristic is a GlcNAc or sialic acid residue and the step of identifying comprises determining whether the sample produces a $^1H$ signal corresponding to an acetyl methyl nucleus of a GlcNAc or sialic acid residue.

16. The method of claim 1, wherein the structural characteristic is a sialic acid residue and the step of identifying comprises determining whether the sample produces a $^1H$ signal corresponding to an axial or equatorial H3 nucleus of a sialic acid residue.

17. The method of claim 1, wherein the structural characteristic is a sialic acid residue with an α2-3 linkage and the step of identifying comprises determining whether the sample produces a $^1H$ signal corresponding to an axial H3 nucleus of a sialic acid residue.

18. The method of claim 1, wherein the structural characteristic is a sialic acid residue with an α2-6 linkage and the step of identifying comprises determining whether the sample produces a $^1H$ signal corresponding to an axial H3 nucleus of a sialic acid residue.

19. The method of claim 1, wherein the structural characteristic is di- or tri-acetylated NeuAc and the step of identifying comprises determining whether the sample produces a $^1H$ signal with a chemical shift at ca. 2.15 ppm.

20. The method of claim 1, wherein the structural characteristic is a fucose residue and the step of identifying comprises determining whether the sample produces a $^1H$ signal corresponding to a methyl nucleus of a fucose residue.

21. The method of claim 1, wherein the structural characteristic is a sialic acid and the step of identifying comprises determining whether the sample produces a $^1H$-$^1H$ scalar correlation between the H3 axial and H3 equatorial nuclei of a sialic acid.

22. The method of claim 1, wherein the structural characteristic is a mono-antennary Man4 residue and the step of identifying comprises determining whether the sample produces a $^1H$-$^1H$ scalar correlation between the H2 and H3 nuclei of a Man4 residue.

23. The method of claim 1, wherein the structural characteristic is a bi-antennary Man4 residue and the step of identifying comprises determining whether the sample produces a $^1H$-$^1H$ scalar correlation between the H2 and H3 nuclei of a Man4 residue.

24. The method of claim 1, wherein the structural characteristic is a galactose residue in a lactosamine extension and the step of identifying comprises determining the chemical shifts of a $^1H$-$^1H$ scalar correlation between the H1 nucleus and another nucleus of a galactose residue.

25. The method of claim 1, wherein the structural characteristic is a sulfated GlcNac residue and the step of identifying comprises determining the chemical shifts of a $^1H$-$^1H$ scalar correlation between the H6 nucleus and another nucleus of a GlcNac residue.

26. The method of claim 1, wherein the structural characteristic is a phosphorylated mannose residue and the step of identifying comprises determining the chemical shifts of a $^1H$-$^1H$ scalar correlation between the H6 nucleus and another nucleus of a mannose residue.

27. The method of claim 1, wherein the structural characteristic is a core fucose residue and the step of identifying comprises determining the chemical shifts of a $^1H$-$^{13}C$ scalar correlation for the anomeric nucleus of a G1cNAc2 residue.

28. The method of claim 1, wherein the structural characteristic is a sialic acid residue and the step of identifying comprises determining whether the sample produces a $^1H$-$^{13}C$ scalar correlation with chemical shifts corresponding to an axial H3 nucleus of a sialic acid residue.

29. The method of claim 1, wherein the structural characteristic is a sialic acid residue and the step of identifying comprises determining whether the sample produces a $^1H$-$^{13}C$ scalar correlation with chemical shifts corresponding to an equatorial H3 nucleus of a sialic acid residue.

30. The method of claim 1, wherein the structural characteristic is an acetylated sialic acid residue and the step of identifying comprises determining the $^1H$ chemical shift of a $^1H$-$^{13}C$ scalar correlation of the H7, H8 and/or H9 nuclei of a sialic acid residue.

31. The method of claim 1, wherein the structural characteristic is a Man4 residue and the step of identifying comprises determining the chemical shifts of a $^1H$-$^{13}C$ scalar correlation corresponding to an anomeric nucleus of a Man4 residue.

32. The method of claim 1, wherein the structural characteristic is a mono- or bi-antennary Man4 residue and the step of determining comprises determining whether the Man4 residue is mono-antennary or bi-antennary based on the chemical shifts of the $^1H$-$^{13}C$ scalar correlation.

33. The method of claim 1, wherein the structural characteristic is a Man4' residue and the step of identifying comprises determining whether the sample produces a $^1H$-$^{13}C$ scalar correlation with chemical shifts corresponding to an anomeric nucleus of a Man4' residue.

34. The method of claim 1, wherein the structural characteristic is a mono- or bi-antennary Man4' residue and the step of determining comprises determining whether the Man4' residue is mono-antennary or bi-antennary based on the chemical shifts of the $^1H$-$^{13}C$ scalar correlation.

35. The method of claim 1, wherein the structural characteristic is a GlcNAc1 residue and the step of identifying comprises determining whether the sample produces a $^1H$-$^{13}C$ scalar correlation with chemical shifts corresponding to an anomeric nucleus of a GlcNAc1 residue.

36. The method of claim 1, wherein the structural characteristic is a GlcNAc2 residue and the step of identifying comprises determining whether the sample produces a $^1H$-$^{13}C$ scalar correlation with chemical shifts corresponding to an anomeric nucleus of a GlcNAc2 residue.

37. The method of claim 1, wherein the structural characteristic is a Man3 residue and the step of identifying comprises determining whether the sample produces a $^1H$-$^{13}C$ scalar correlation with chemical shifts corresponding to an anomeric nucleus of a Man3 residue.

38. The method of claim 1, wherein the structural characteristic is a GlcNac residue with a β(1-2) linkage to mannose and the step of identifying comprises determining whether the sample produces a $^1H$-$^{13}C$ scalar correlation with chemical shifts corresponding to an anomeric nucleus of a GlcNac residue with a β(1-2) linkage to mannose.

39. The method of claim 1, wherein the structural characteristic is a GlcNAc residue with a β(1-4) or β(1-6) linkage to mannose and the step of identifying comprises determining whether the sample produces a $^1H$-$^{13}C$ scalar correlation with chemical shifts corresponding to an anomeric nucleus of a GlcNAc residue with a β(1-4) or β(1-6) linkage to mannose.

40. The method of claim 1, wherein the structural characteristic is a GlcNAc residue in a lactosamine extension and the step of identifying comprises determining whether the sample produces a $^1$H-$^{13}$C scalar correlation with chemical shifts corresponding to an anomeric nucleus of a GlcNac residue in a lactosamine extension.

41. The method of claim 1, wherein the structural characteristic is an unsubstitued galactose residue and the step of identifying comprises determining whether the sample produces a $^1$H-$^{13}$C scalar correlation with chemical shifts corresponding to an anomeric nucleus of an unsubstitued galactose residue.

42. The method of claim 1, wherein the structural characteristic is a galactose residue with an α(2-3) sialic acid attached and the step of identifying comprises determining whether the sample produces a $^1$H-$^{13}$C scalar correlation with chemical shifts corresponding to an anomeric nucleus of a galactose residue with an α(2-3) sialic acid attached.

43. The method of claim 1, wherein the structural characteristic is a galactose residue with an α(2-6) sialic acid attached and the step of identifying comprises determining whether the sample produces a $^1$H-$^{13}$C scalar correlation with chemical shifts corresponding to an anomeric nucleus of a galactose residue with an α(2-6) sialic acid attached.

44. The method of claim 1, wherein the structural characteristic is a galactose residue in a lactosamine extension and the step of identifying comprises determining whether the sample produces a $^1$H-$^{13}$C scalar correlation with chemical shifts corresponding to an anomeric nucleus of a galactose residue in a lactosamine extension.

45. The method of claim 1, wherein the structural characteristic is an oligomannose structure and the step of identifying comprises determining whether the sample produces a $^1$H-$^{13}$C scalar correlation with chemical shifts corresponding to an anomeric nucleus of an oligomannose structure.

46. The method of claim 1, wherein the structural characteristic is a core fucose residue and the step of identifying comprises determining whether the sample produces a $^1$H-$^{13}$C scalar correlation with chemical shifts corresponding to an anomeric nucleus of a core fucose residue.

47. The method of claim 1, wherein the structural characteristic is a core fucose residue and the step of identifying comprises determining whether the sample produces a $^1$H-$^{13}$C scalar correlation with chemical shifts corresponding to a methyl nucleus of a core fucose residue.

48. The method of claim 1, wherein the structural characteristic is an antennary fucose residue and the step of identifying comprises determining whether the sample produces a $^1$H-$^{13}$C scalar correlation with chemical shifts corresponding to a methyl nucleus of an antennary fucose residue.

49. The method of claim 1, wherein the structural characteristic is a label attached to GlcNAc1 and the step of identifying comprises determining whether the sample produces a $^1$H signal corresponding to GlcNAc1a H1.

50. The method of claim 1, wherein the structural characteristic is a label attached to GlcNAc1 and the step of identifying comprises determining whether the sample produces a split $^1$H-$^1$H scalar correlation corresponding to fucose H1/H2, H1/H3 or —CH$_3$/H5 nuclei.

51. The method of claim 1, wherein the structural characteristic is a label attached to GlcNAc1 and the step of identifying comprises determining whether the sample produces a $^1$H-$^{13}$C scalar correlation corresponding to an anomeric nucleus of GlcNAc1a or GlcNAc1β.

52. The method of claim 1, wherein the structural characteristic is a label attached to GlcNAc1 and the step of identifying comprises determining the chemical shifts of a $^1$H-$^{13}$C scalar correlation corresponding to an anomeric nucleus of a GlcNAc2 or Man3 residue.

53. The method of claim 1, wherein the structural characteristic is a label attached to GlcNAc1 and the step of identifying comprises determining whether the sample produces a split $^1$H-$^{13}$C scalar correlation corresponding to an anomeric fucose nucleus.

54. The method of claim 1, wherein the structural characteristic is a label attached to GlcNAc1 and the step of identifying comprises determining whether the sample produces a split $^1$H-$^{13}$C scalar correlation corresponding to a methyl fucose nucleus.

* * * * *